(12) United States Patent
Popov

(10) Patent No.: US 7,731,730 B2
(45) Date of Patent: Jun. 8, 2010

(54) SAFETY TROCAR ASSEMBLY

(76) Inventor: Sergey Popov, P.O. Box 4583, Be'er Sheva (IL) 84144

( * ) Notice: Subject to any disclaimer, the term of this patent is extended or adjusted under 35 U.S.C. 154(b) by 1217 days.

(21) Appl. No.: 11/028,502

(22) Filed: Jan. 4, 2005

(65) Prior Publication Data

US 2006/0149302 A1    Jul. 6, 2006

Related U.S. Application Data

(62) Division of application No. 09/936,741, filed as application No. PCT/IB00/00408 on Mar. 14, 2000, now Pat. No. 6,837,874.

(30) Foreign Application Priority Data

Mar. 15, 1999    (IL) .................................... 128989

(51) Int. Cl.
*A61B 17/34* (2006.01)
(52) U.S. Cl. .................. 606/185; 606/184; 606/181

(58) Field of Classification Search ......... 606/167–173, 606/181–185; 604/523, 264, 165
See application file for complete search history.

(56) References Cited

U.S. PATENT DOCUMENTS

| | | | | |
|---|---|---|---|---|
| 3,805,793 A | * | 4/1974 | Wright | 604/22 |
| 4,535,773 A | * | 8/1985 | Yoon | 606/185 |
| 4,601,710 A | * | 7/1986 | Moll | 604/164.12 |
| 4,931,042 A | * | 6/1990 | Holmes et al. | 604/164.12 |
| 4,943,280 A | * | 7/1990 | Lander | 604/256 |
| 5,066,288 A | * | 11/1991 | Deniega et al. | 604/274 |
| 5,275,583 A | * | 1/1994 | Crainich | 604/264 |
| 5,591,190 A | * | 1/1997 | Yoon | 606/185 |
| 5,807,402 A | * | 9/1998 | Yoon | 606/185 |
| 6,063,099 A | * | 5/2000 | Danks et al. | 606/185 |

* cited by examiner

*Primary Examiner*—Todd E Manahan
*Assistant Examiner*—Katherine M Dowe
(74) *Attorney, Agent, or Firm*—Daniel J. Swirsky; AlphaPatent Associates Ltd.

(57) ABSTRACT

A trocar assembly including a low-profile retractable shield deployable adjacent to a cutting element with a cross-sectional area which is small relative to the total cross-section of the assembly.

6 Claims, 18 Drawing Sheets

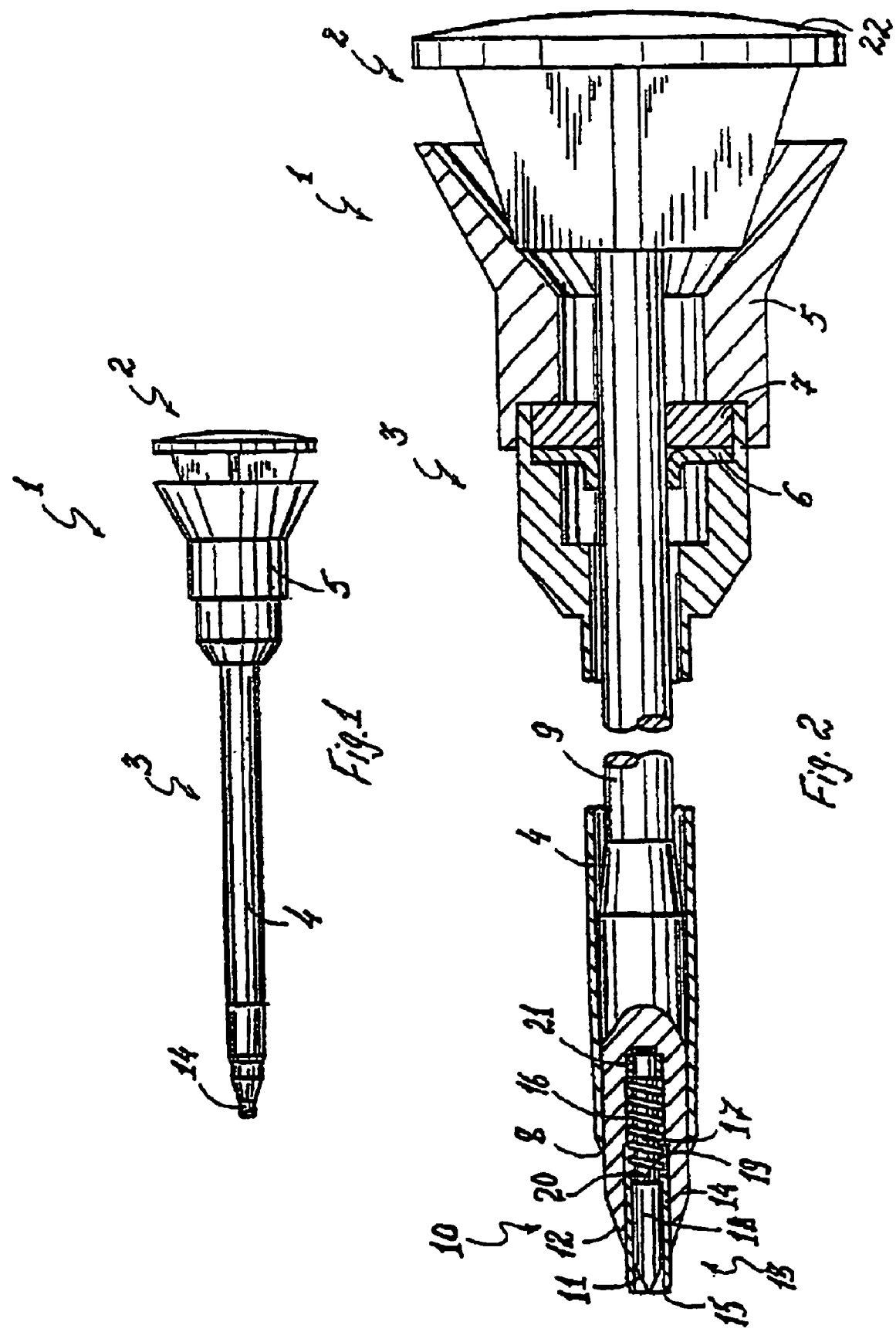

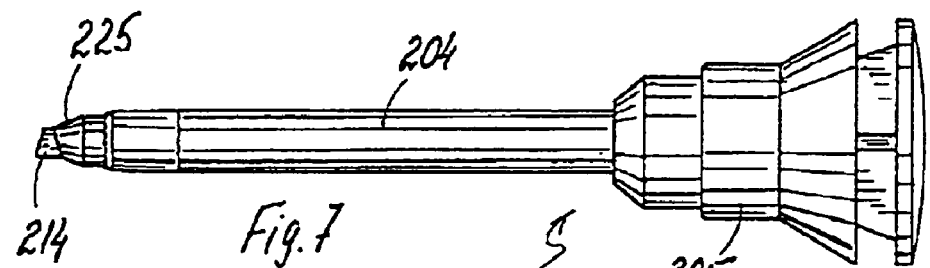
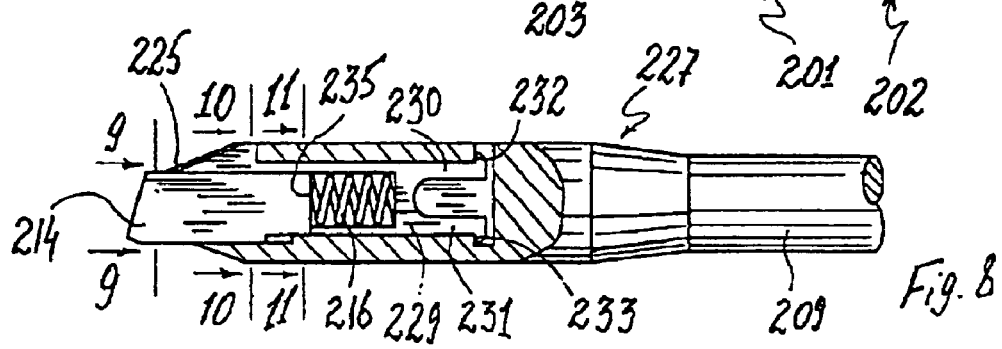
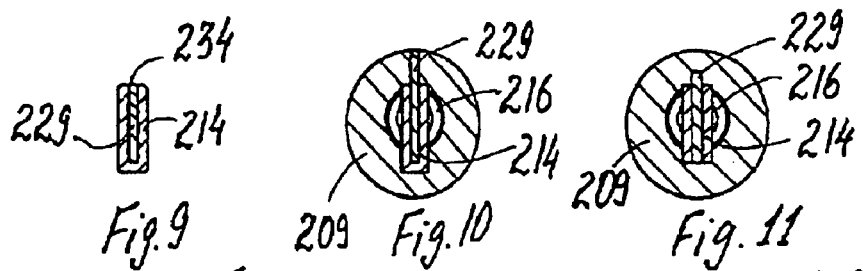
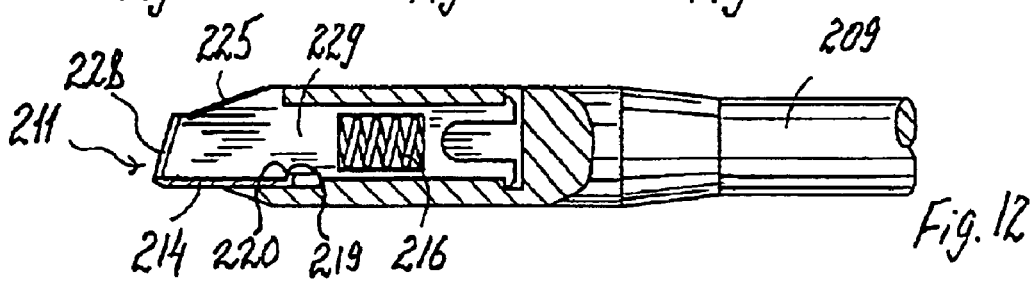
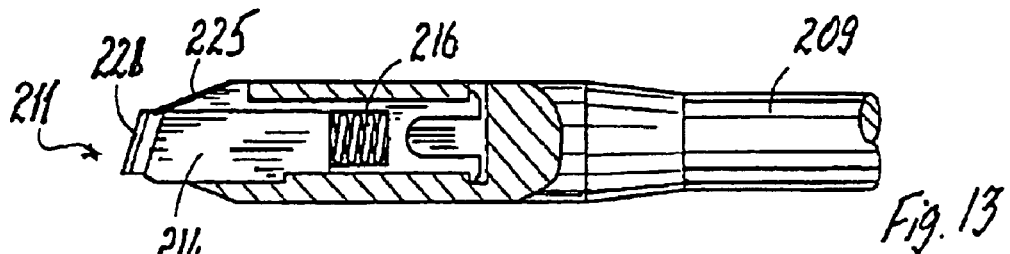
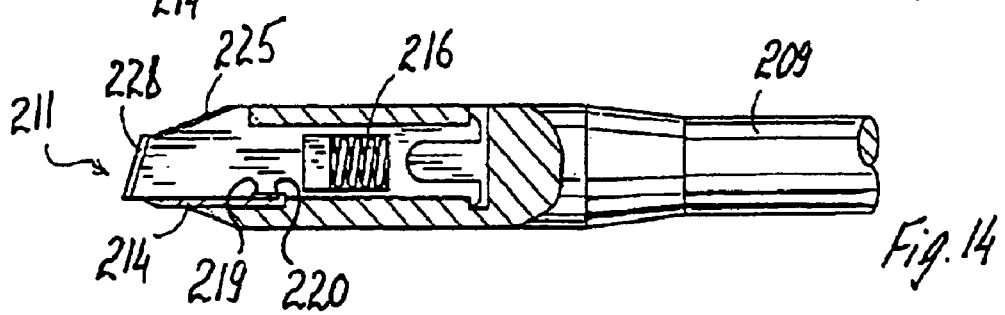

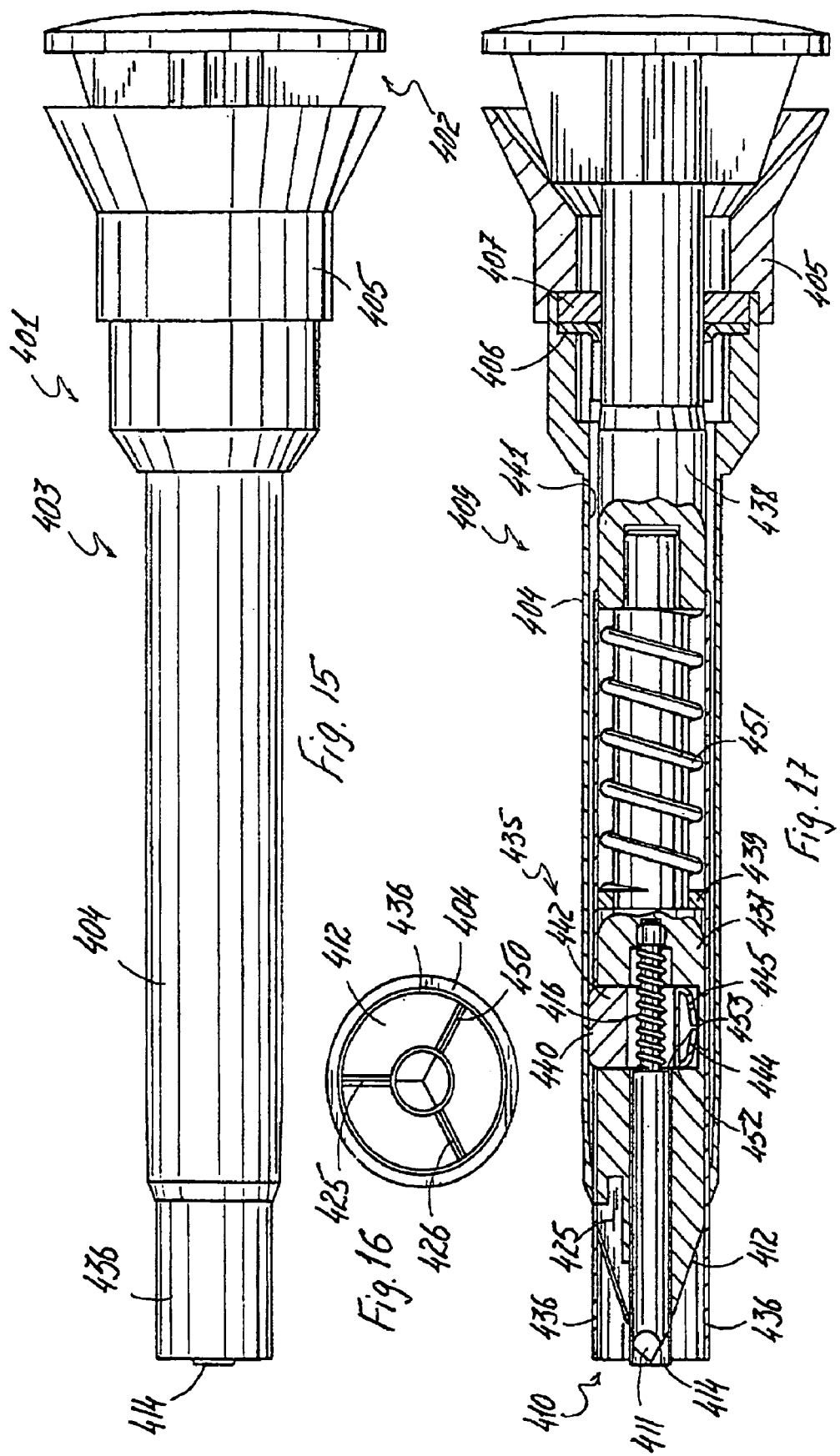

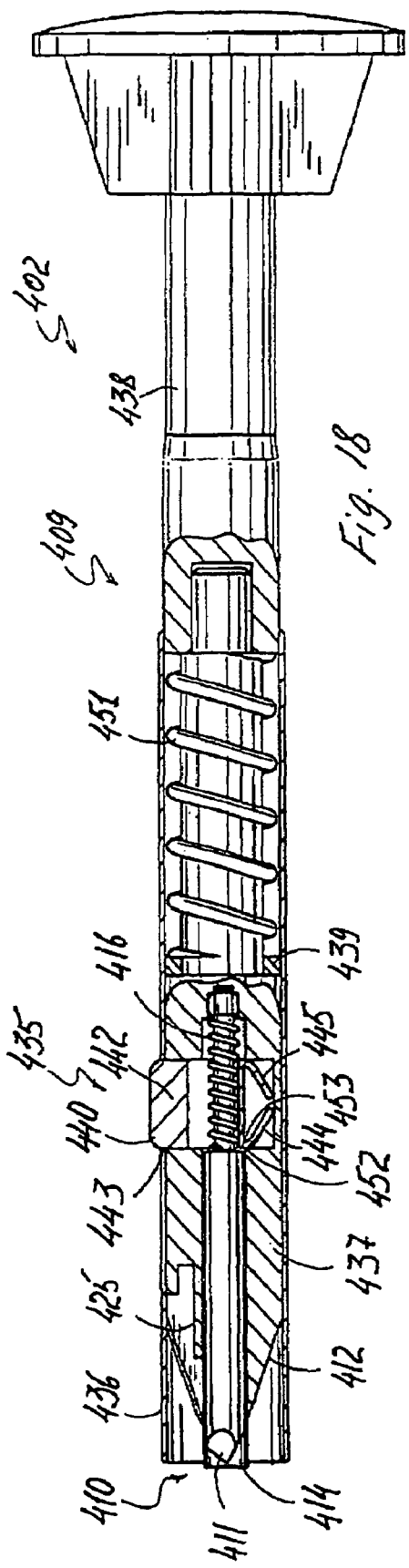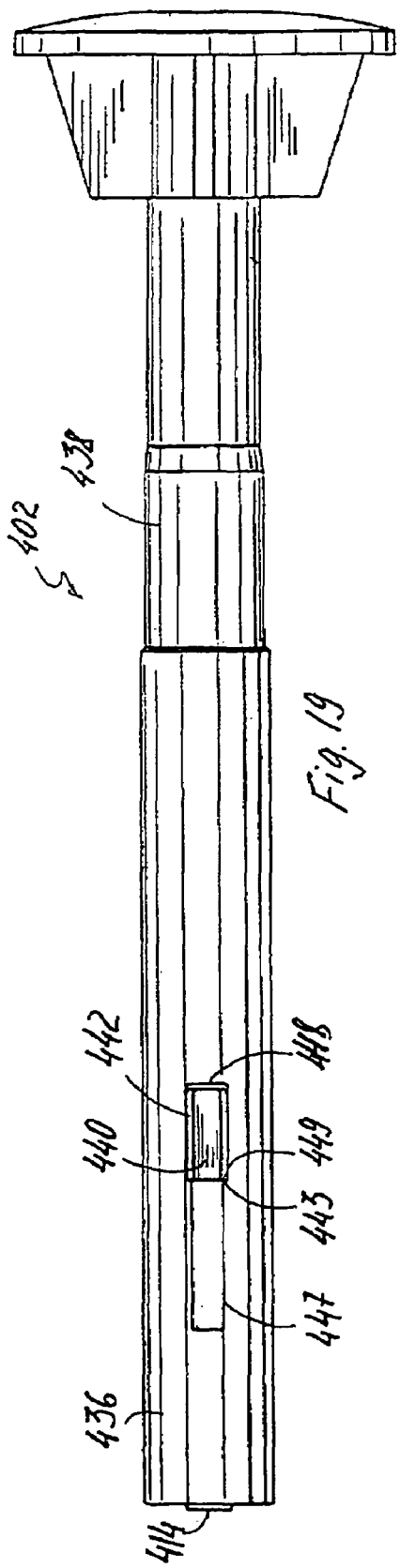

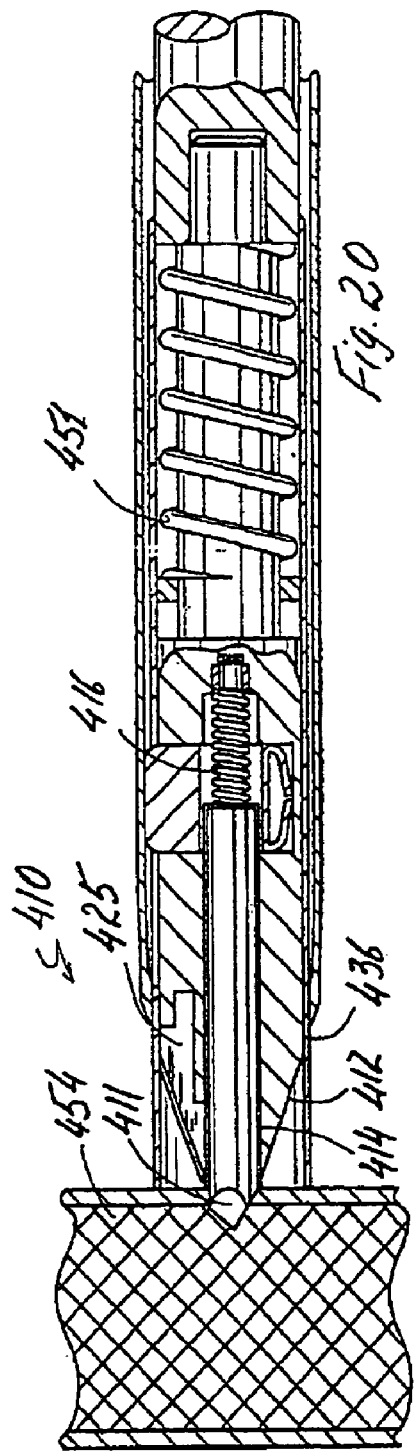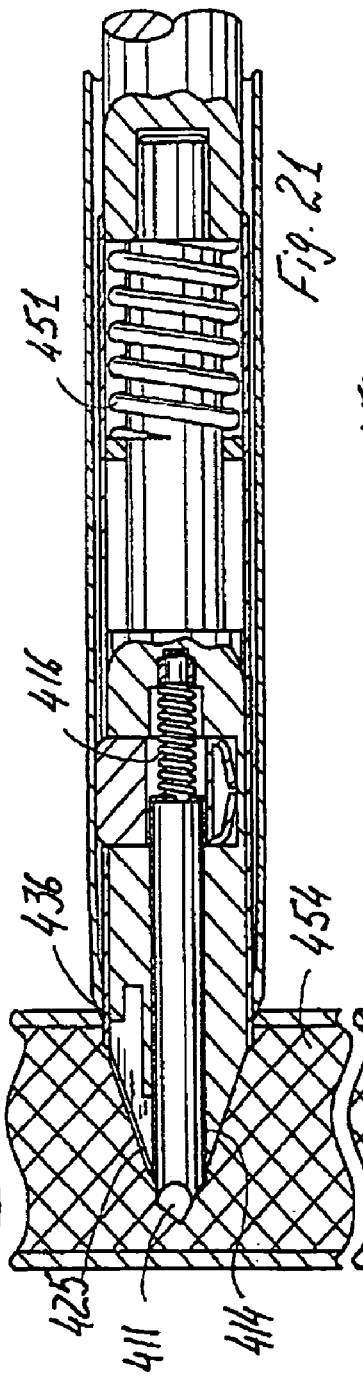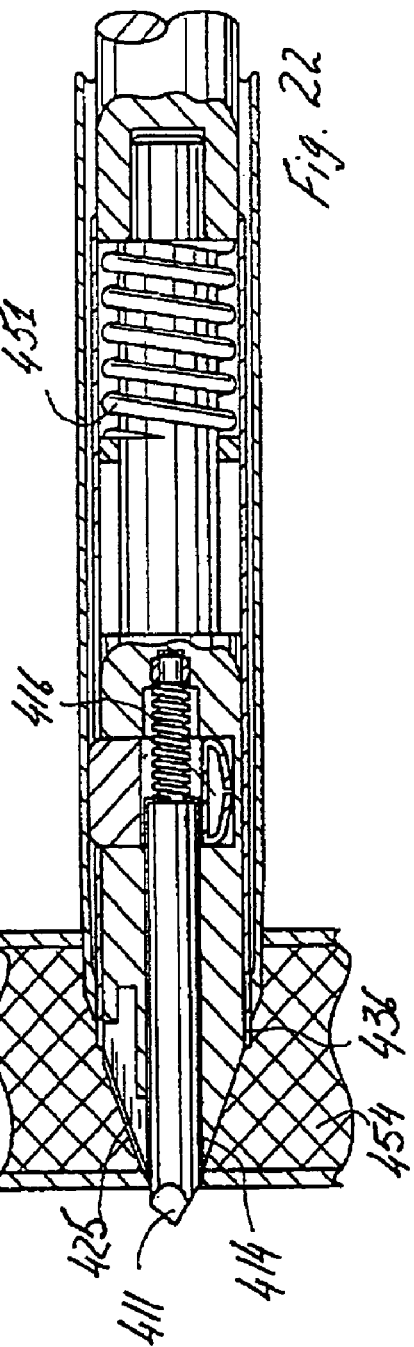

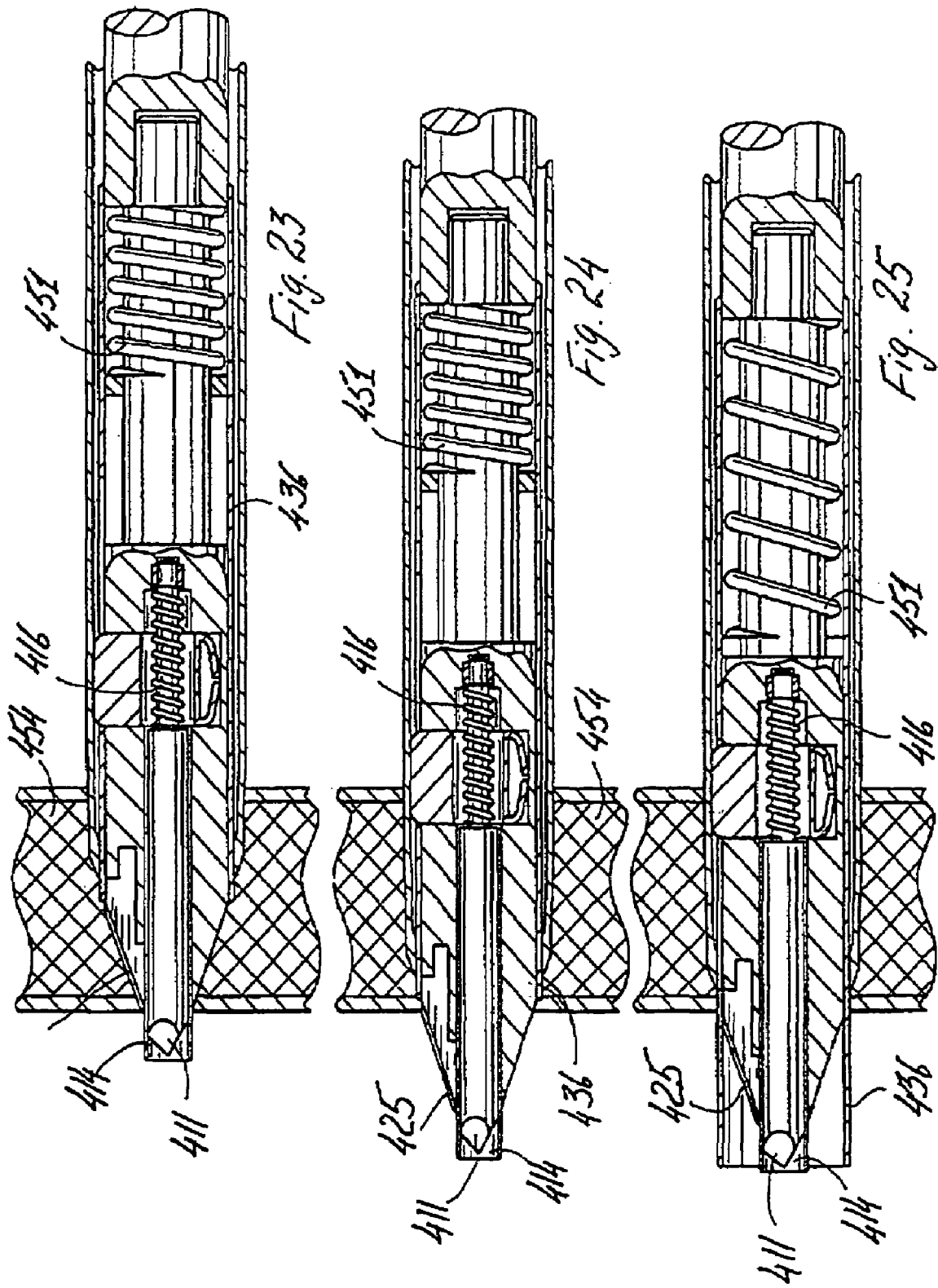

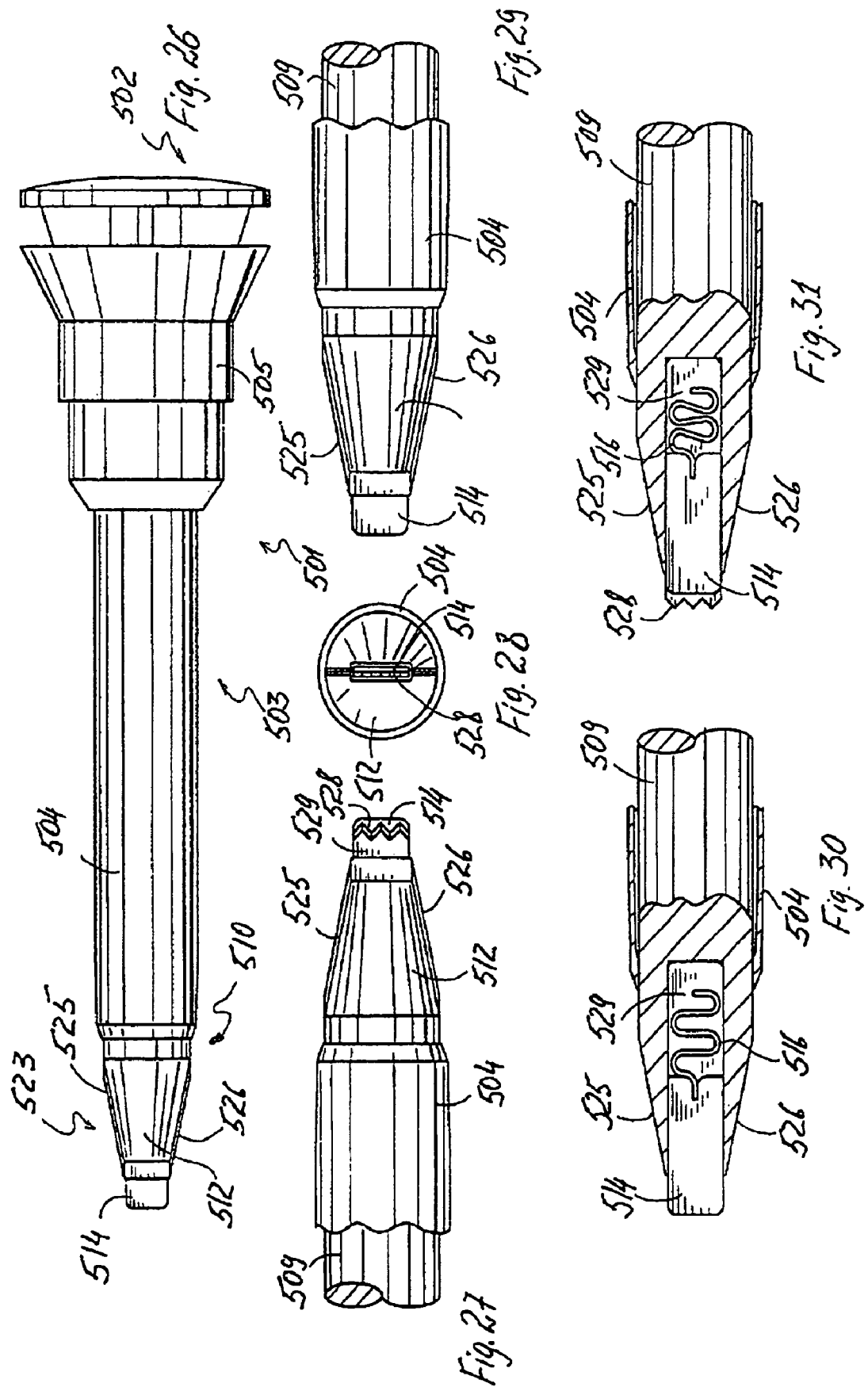

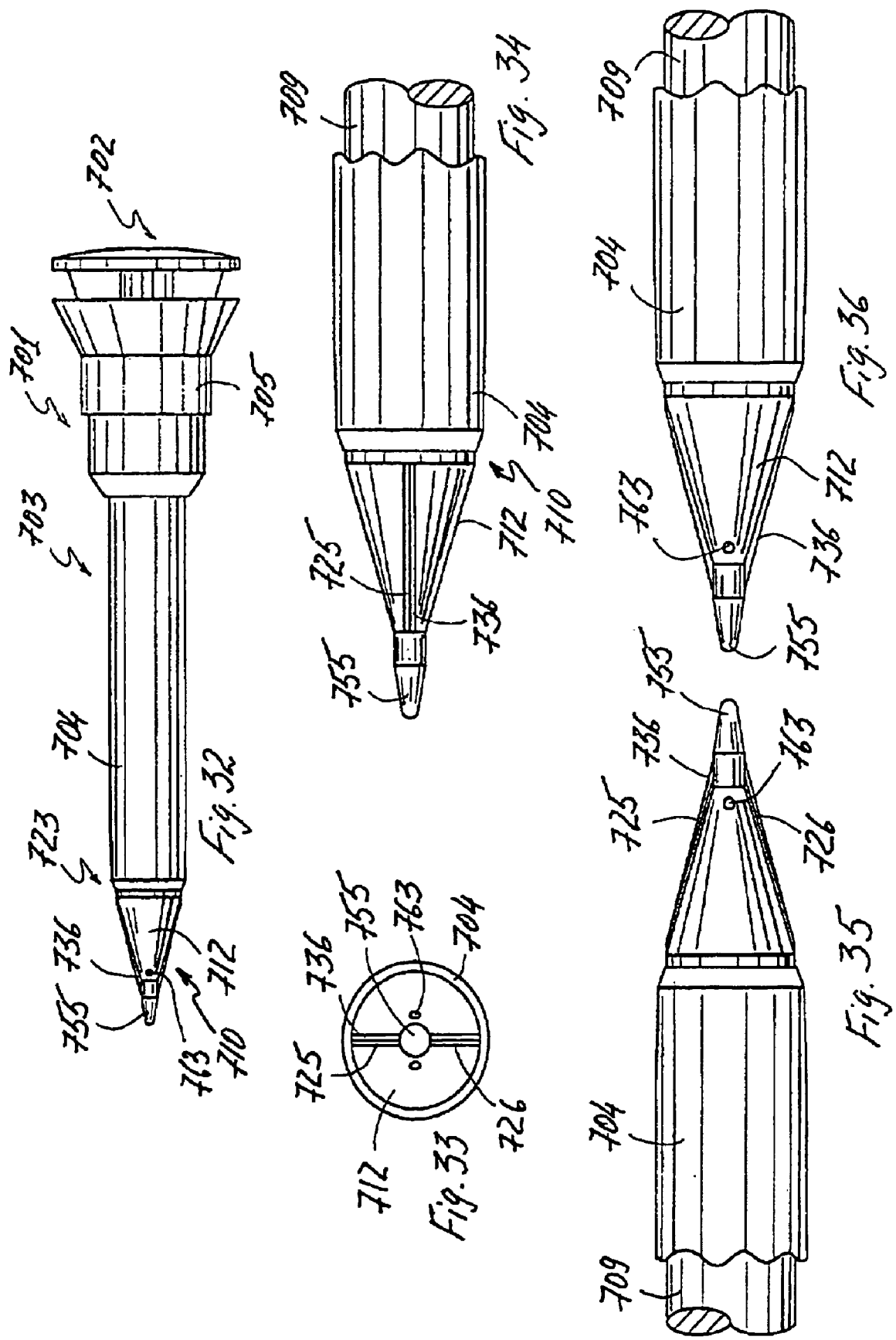

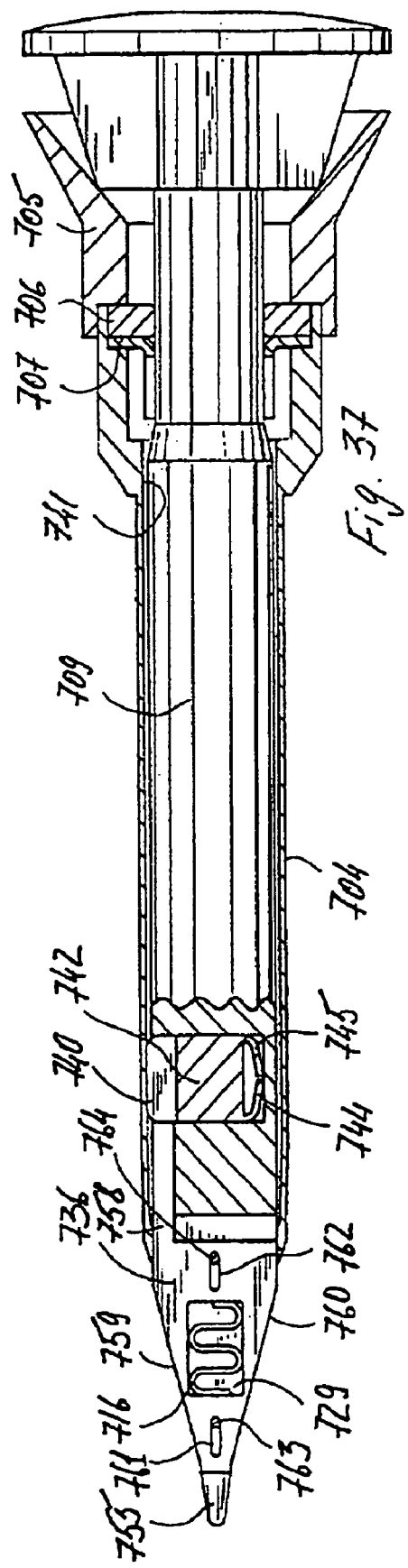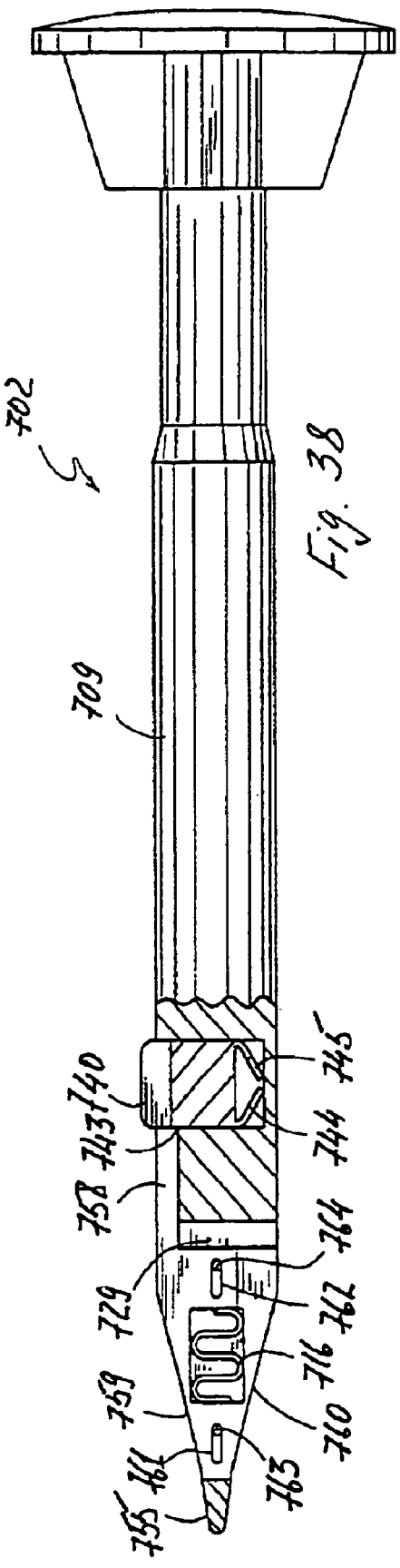

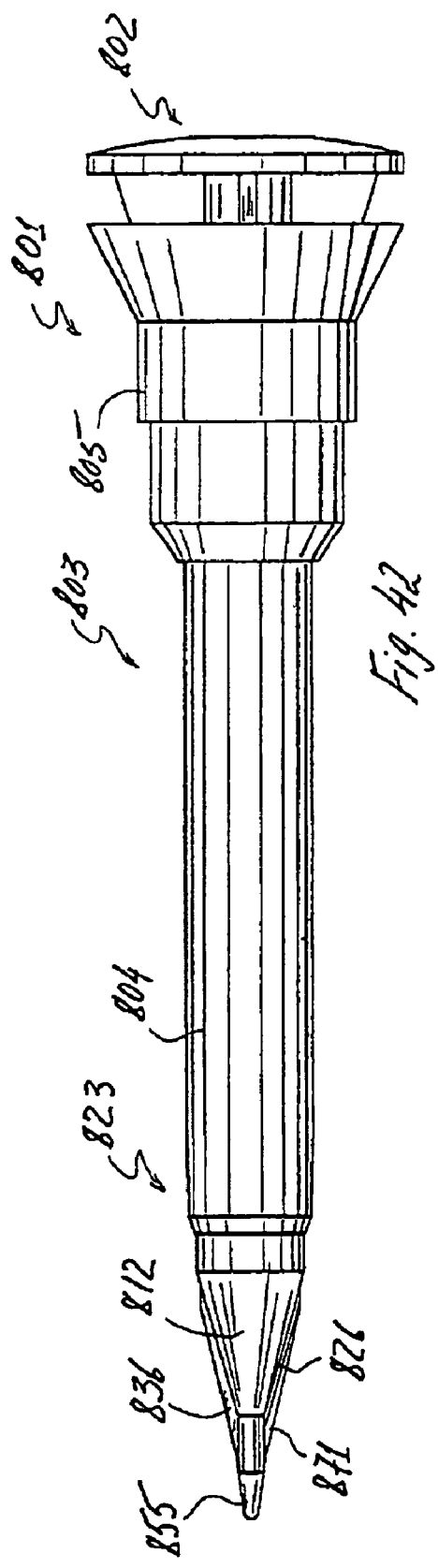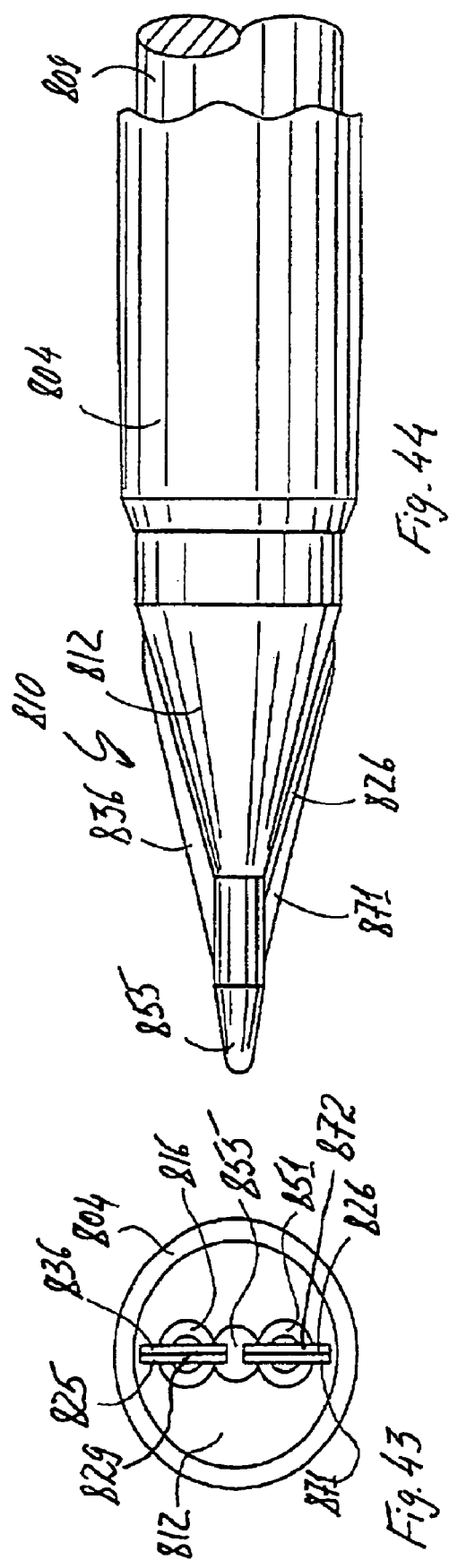
Fig. 42
Fig. 43
Fig. 44

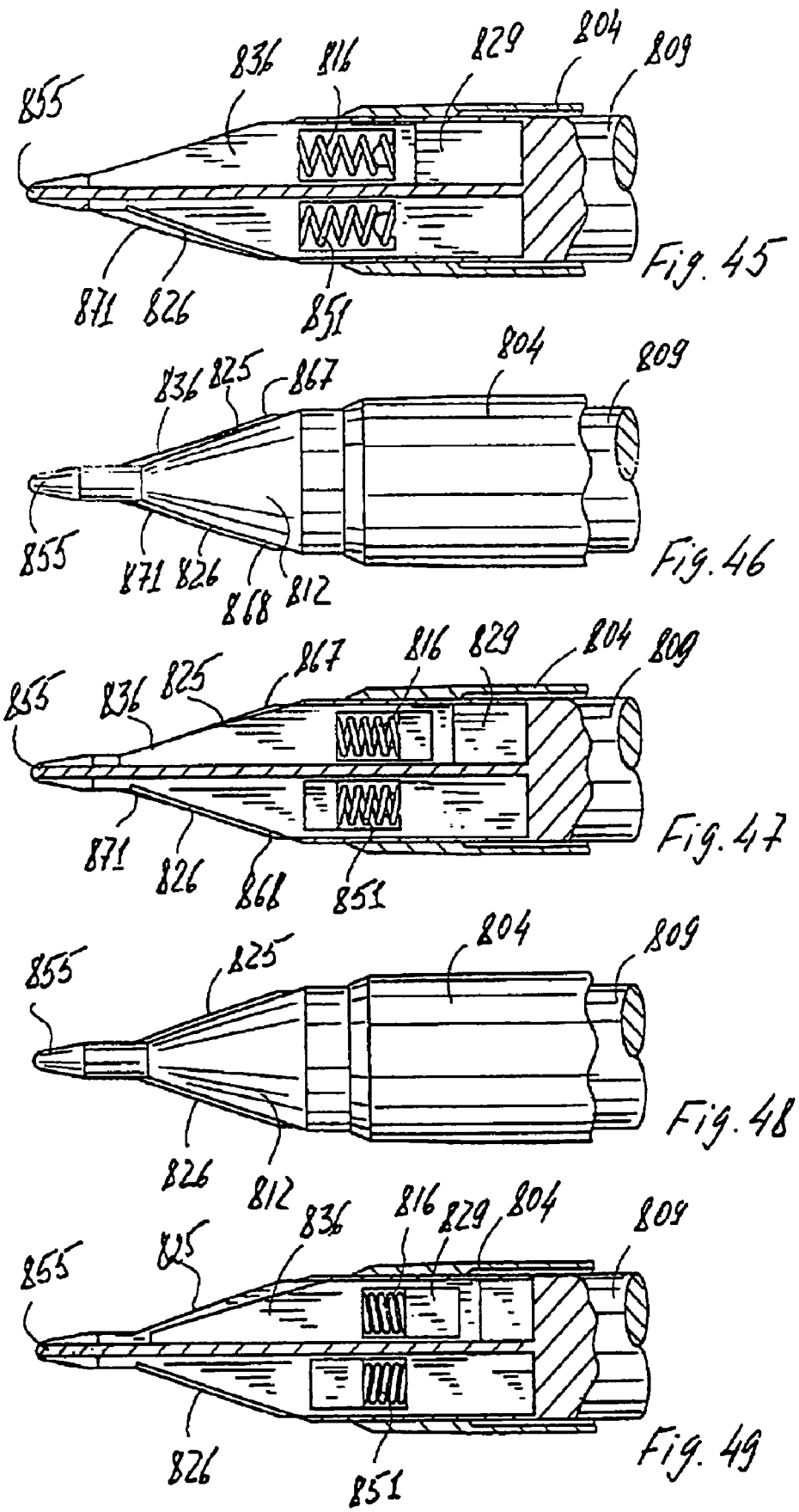

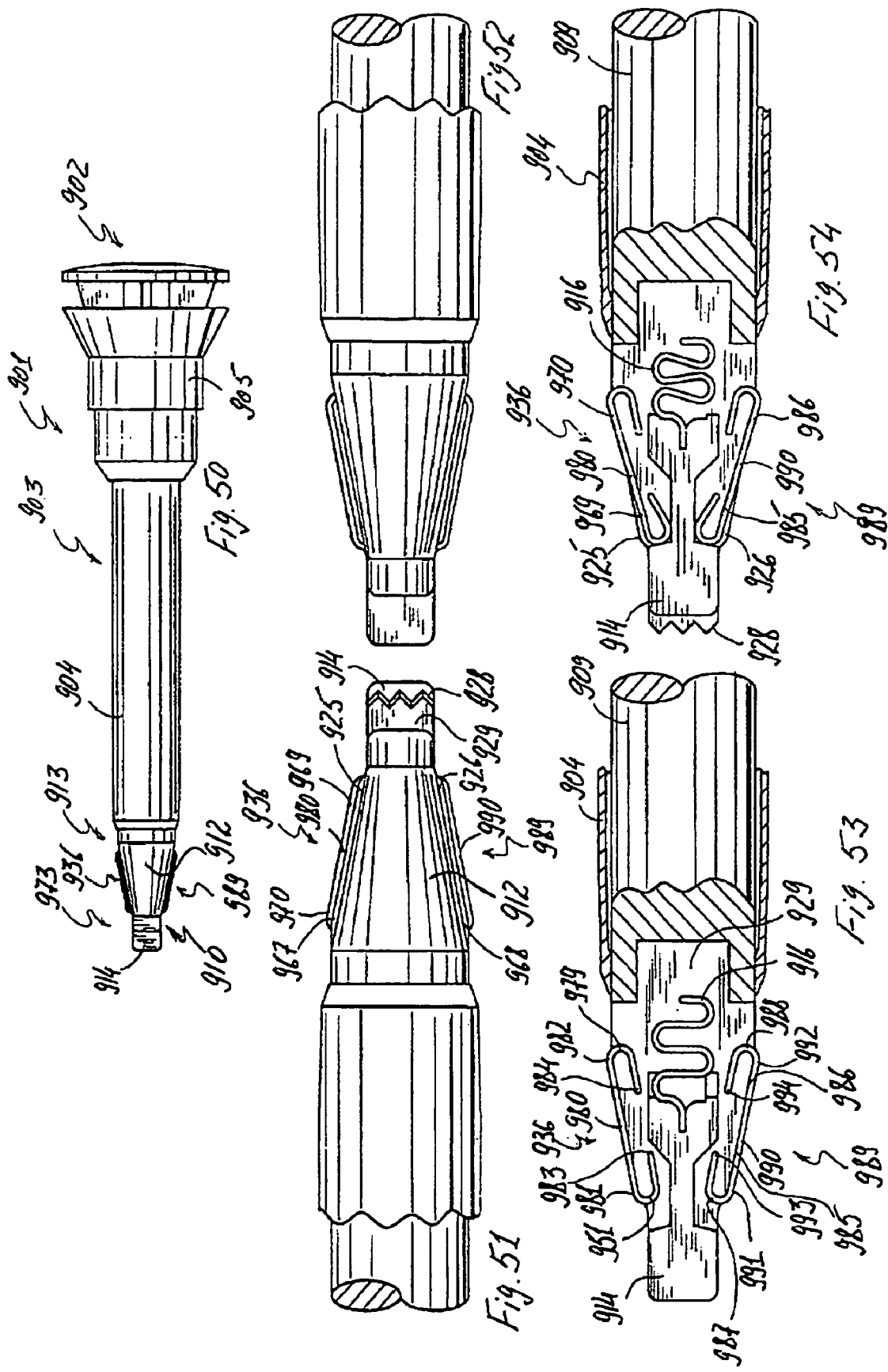

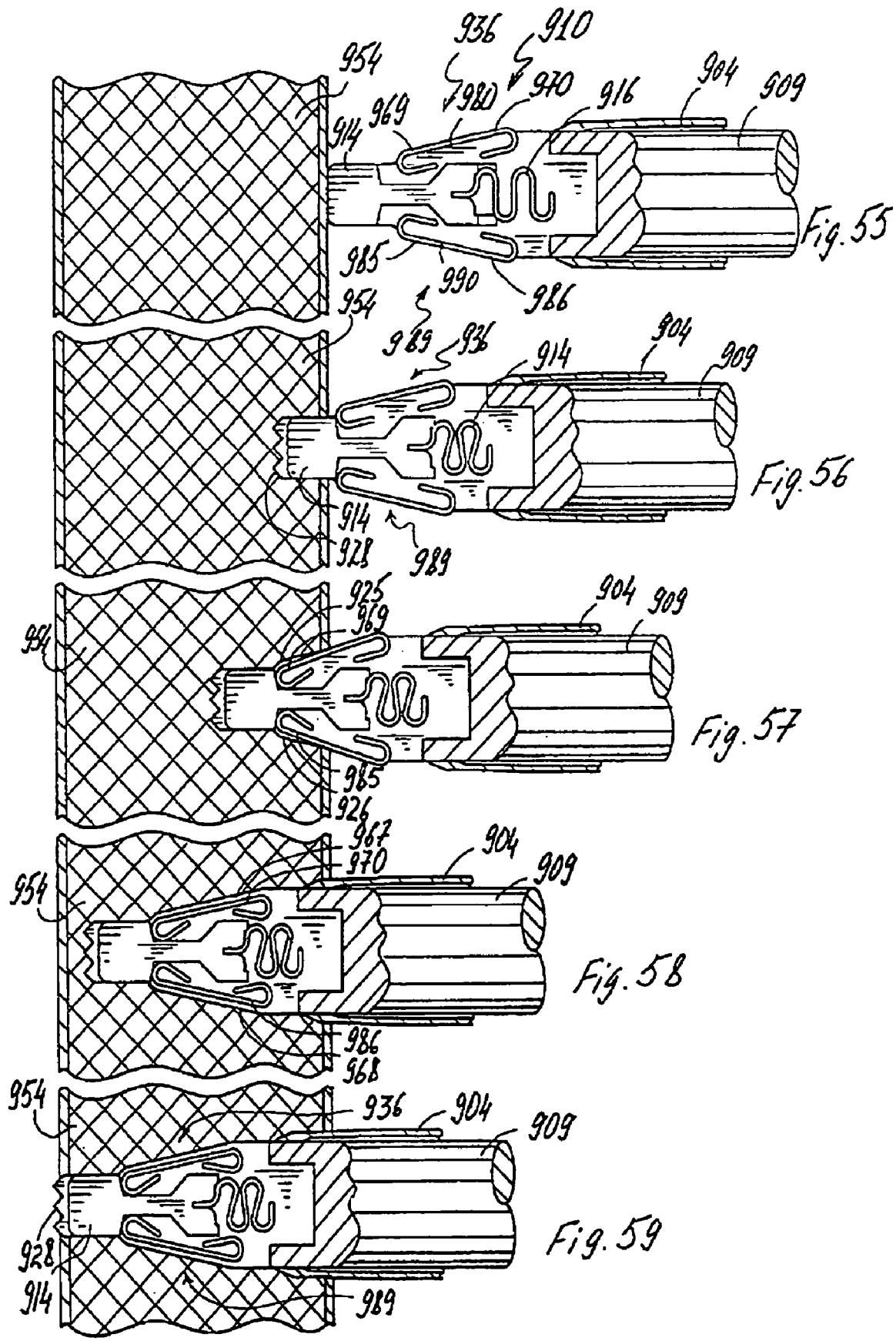

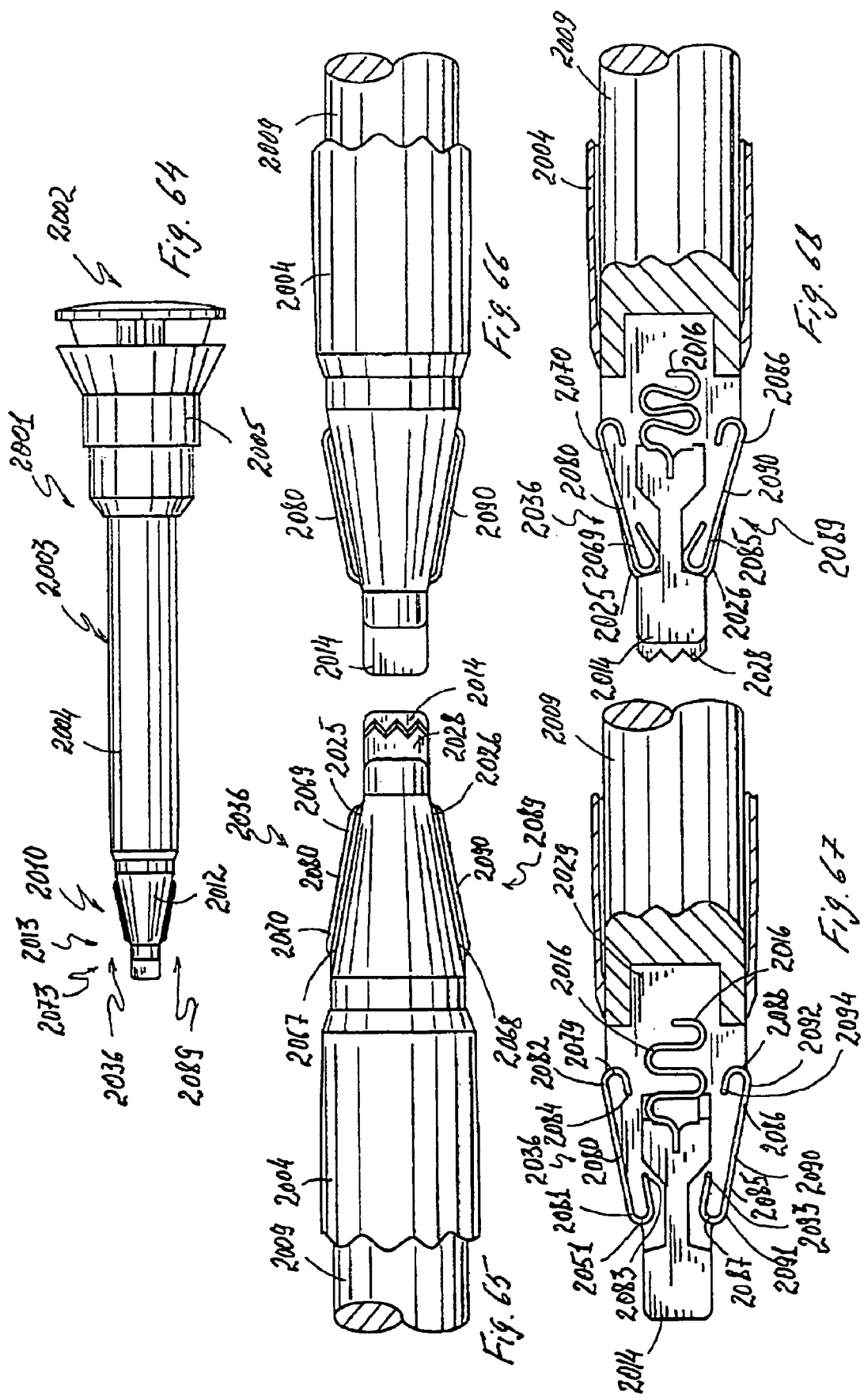

SAFETY TROCAR ASSEMBLY

CROSS-REFERENCE TO RELATED APPLICATIONS

This application is a divisional application of U.S. patent application Ser. No. 09/936,741, filed Sep. 13, 2001, now U.S. Pat. No. 6,837,874 which was a U.S. National Phase Patent Application under 35 U.S.C. 371 of PCT International Application No. PCT/IB00/00408, which has an international filing date of Mar. 14, 2000, and which claims priority from Israel Patent Application No. 128,989, filed Mar. 15, 1999, all incorporated herein by reference in their entirety.

FIELD OF THE INVENTION

The present invention relates to medical equipment, in particular to trocar and similar devices used in surgical procedures and intended for their improvement.

BACKGROUND OF THE PRIOR ART

Trocars are used in medicine for making orifices and trocar port placement in body cavity walls used further for diagnostic or surgical instrument insertion into body cavity. Trocar insertion into body cavity can be accompanied with internal organ injury. To prevent such a complication, the trocars are equipped with various protectors of piercing-cutting means. However, all known solutions do not eliminate the problem of internal organ injuries.

The safety trocar penetrating instrument is known from the U.S. Pat. No. 5,591,190, comprising port unit and trocar unit with obturator having piercing-cutting means. The device is equipped with protector for piercing-cutting means made as a tubular shield situated between obturator and tubular cannula of port unit and movable relative to obturator from the extended position when it encloses piercing-cutting means and prevents it from any contact, to the retracted one, when piercing-cutting means is open and can perforate the body cavity wall. Such a protector advances to the extended position when the resistance of body cavity wall drops after the exposed piercing, cutting means has already entered the body cavity, i.e. after internal organs could have ready been injured.

Another trocar and cannula assembly are known from the U.S. Pat. No. 5,246,425, wherein a tip protector comprises a plurality of projections which, by the authors' idea should be displaced into an extended position before the piercing apex has been fully inserted into the body cavity. However, such mechanism leads to inevitable injury of body cavity wall, increased resistance to the device advance, the device advance in jerks, and high probability of protector jamming. Moreover, when these members pass through fibrous anatomical structures: aponeuroses, fascias, muscles, the structure fibers enter either the projections, or between the projections and tip. Further device advance is possible solely by rupturing these fibers which, in its turn, results in increased tissue injury and in the device hindered advance.

The tissue fibers incorporated between projections and tip can jam protector in the retracted position. In this case the jeopardy of internal body injury is even higher than by the performance of a trocar non-equipped with protector, since a surgeon, being sure of the device safety, operates with less caution.

A trocar with a shield is disclosed by U.S. Pat. No. 5,797,943. The geometry of the descried shield should, by the authors' opinion, ensure successive protection of various zones in piercing-cutting means practically simultaneously with their penetration to the body cavity.

However, shield members have such sizes, shape, arrangement and contact zone with body cavity wall that they generate considerable resistance between the shield and the body cavity wall tissues, and the latter holds the shield in totally retracted position, up to the shield complete removal beyond the bounds of body cavity wall, which means that no successive protection of piercing-cutting members takes place as they enter the body cavity.

Similar demerit is found in U.S. Pat. Nos. 5,690,663, 5,709,671. A trocar, having improved tip configuration is disclosed by U.S. Pat. No. 5,709,671, where distal edge of tubular cannula is made sloping, to facilitate the device passing through body cavity wall. In fact, the surgeon has less difficulties in trocar passing through tissues since sloping edge of cannula operates as a wedge giving the benefit of force, which facilitates tissue rupture by trocar passing. But tissue injury during the trocar performance remains considerable.

SUMMARY OF THE INVENTION

The invention objective is the decrease of internal organ injury risk upon trocar performance.

Another invention objective is increased reliability of protector operation by preventing jamming and engagement of body cavity wall tissues between the members of trocar distal edge.

Another invention objective is decreased tissue injury of body cavity wall.

Another invention objective is facilitated trocar passing through body cavity wall.

Another invention objective is decreased material consumption for the device, design simplification and device low-cost manufacturing.

Another invention objective is independent of each other operation start and finish of cutting members dependable on tissue local biomechanical properties.

Another invention objective is accurate adaptation of orifice sizes in body cavity wall to the cannula diameter.

The above noted objectives are accomplished by a safety trocar assembly having a port unit with elongated obturator removably inserted through the cannula and having a handle on its proximal end and a penetrating end on its distal end. The penetrating end is exposed through the cannula open distal end and has a cutting means, a penetrating apex, and a sloping side wall immovable relative to obturator. The obturator is provided with a protector means having a bias means and a movable penetrating apex shield that in its retracted position opens the penetrating apex and in its extended position closes the penetrating apex preventing it from any contact with patient's organs. In the projection onto transverse plane, the obturator sloping side wall surrounds the penetrating apex shield. It means that the penetrating and, consequently, also the penetrating apex shield have little cross section dimensions in comparison with the obturator. This allows reduction of the resistance of body tissue during penetrating apex shield displacement to its extended position and provides fast acting protection of the penetrating apex immediately after the penetration of penetrating apex distal end into the body cavity, however, before the penetrating end has been fully inserted. Further dilation of the orifice in the body wall is carried out by cutting means located on the sloping side wall. The penetrating apex shield is made tubular of circular or flattened cross section, totally closed or having a slot on one side. The distal edge of this shield forms a fence precluding the introduction, jamming; and engagement of tissue fibers of the body cavity wall between the penetrating apex shield and the penetrating apex as well as between the penetrating apex shield segments. As a result, the injury of body cavity wall is decreased and trocar passing through body cavity wall is facilitated.

According to the present invention, the shield, particularly made plate-shaped and the perimeter of its cross section insignificantly exceeds the perimeter of tissue incision made by the cutting means. Moreover, the height of this plate-shaped shield (the plate thickness) amounts 0.4 to 2 mm for obturator with outer diameter 10 to 12.5 mm and 0.4 to 1.2 mm for obturator with outer diameter 5 to 6.5 mm. This shield is a fast acting protector entering the tissue incision without substantial resistance of tissue incision edges and enabling the shield entry the body cavity immediately after entry there the cutting means. As a result, the risk of patient internal organ injury is significantly decreased.

In version embodiment, a safety trocar assembly comprises a penetrating means with at least two penetrating zones and a protector means with independent protector members, made as shields, for independent protection of each of said penetrating zones, and a resilient bias means for each of the protector members. This protects the penetrating zone (knife) which enters the body cavity independently of other penetrating zones (knives) which have not yet entered the body cavity and continue to cut the tissue. In version embodiment, there are distal and proximal penetrating zones provided with a distal and a proximal independent shield, respectively. The distal penetrating zone is the first one that enters the body cavity and is a main cause of internal organ injury, so its independent and fast protection eliminates trocar procedure complications.

In version embodiment, the displacement of the proximal shield from the extended position to the retracted position demands greater force than identical displacement of the distal shield. That can be achieved by larger rigidity of the bias means (in the form of a spring) of the proximal shield than one of the distal shield. As a result, the proximal penetrating zone forms such final dimensions of orifice that is accurately adapted to the cannula outer diameter. Described penetrating and protector means have so simple a design (for example, making protector and biasing members as a one detail) so as to permit their arrangement in the limits of obturator distal part. Such implementation increases trocar reliability and reduces its manufacturing cost.

BRIEF DESCRIPTION OF THE DRAWINGS

Various embodiments of the safety trocar assembly of the subject application will be described below with reference to the following drawings wherein:

FIG. 1 is a perspective view of trocar assembly with tubular penetrating apex shield.

FIG. 2 is a longitudinal section of trocar assembly of the FIG. 1.

FIG. 7 is a perspective view of trocar assembly with groove penetrating apex shield.

FIG. 8 is a longitudinal section of distal part of trocar assembly of the FIG. 7 with groove shield in extended position.

FIGS. 9-11 are sections of trocar assembly of the FIG. 8 on the levels 9-9, 10-10, 11-11, respectively.

FIG. 12 is a longitudinal section of distal part of trocar assembly and groove shield of the FIG. 8.

FIG. 13 is a longitudinal section of distal part of trocar assembly of the FIG. 7 with groove shield in retracted position.

FIG. 14 is a longitudinal section of distal part of trocar assembly and groove shield of the FIG. 13.

FIG. 15 is a perspective view of trocar assembly with two independent tubular shields.

FIG. 16 is a left-hand view of device of the FIG. 15.

FIG. 17 is a longitudinal section of device of the FIG. 15.

FIG. 18 is a longitudinal view of trocar unit of device of the FIG. 17.

FIG. 19 is a perspective view of the trocar unit of the FIG. 18.

FIGS. 20-25 demonstrate successive changes in mutual positions of the shields at the stages of trocar penetrating end passing though body cavity wall.

FIG. 26 is a perspective view of trocar assembly with low profile protector.

FIG. 27 is a knife-side view of distal part of trocar assembly of the FIG. 26.

FIG. 28 is a left-hand view of the trocar assembly of FIG. 26.

FIG. 29 is a protector-side view of distal part of trocar assembly of the FIG. 26.

FIG. 30 is a longitudinal section of distal part trocar assembly of the FIG. 29.

FIG. 31 is a longitudinal section of the distal part of trocar assembly of the FIG. 29 with protector displaced to retracted position.

FIG. 32 is a perspective view of trocar assembly with low profile inverted shield.

FIG. 33 is left-hand view of device of the FIG. 32.

FIG. 34 is a top view of distal part of device of the FIG. 32.

FIG. 35 is a knife-side view of distal part of device of the FIG. 32.

FIG. 36 is a shield-side view of distal part of device of the FIG. 32.

FIG. 37 is a longitudinal view of device of the FIG. 32.

FIG. 38 is a view of trocar unit of device of the FIG. 32.

FIG. 42 is a perspective view of trocar assembly with two independent low profile inverted shields.

FIG. 43 is a left-hand view of device of the FIG. 42.

FIG. 44 is an enlarged distal part of device of the FIG. 42.

FIG. 45 is a longitudinal section of distal part of device of the FIG. 42.

FIG. 46 is a distal part of device of the FIG. 42 with shields between extended and retracted positions.

FIG. 47 is a longitudinal section of device of the FIG. 46.

FIG. 48 is a distal part of the device of the FIG. 42 with shield in retracted position.

FIG. 49 is a longitudinal section of device of the FIG. 48.

FIG. 50 is a perspective view of safety trocar with three independent shields.

FIGS. 51, 52 are views of distal part of device of the FIG. 50 from knife- and shield-side, respectively.

FIG. 53 is a longitudinal section view of distal part device of the FIG. 50.

FIG. 54 is a longitudinal section view of distal part device of the FIG. 50 with plated shield in retracted position.

FIGS. 55-63 demonstrates positions of shields at various penetration stages of the distal part of FIG. 50 device through body cavity wall.

FIG. 64 is a perspective view of trocar assembly, wherein proximal bias members of lateral shields are made more rigid than distal ones.

FIG. 65 is a knife-side view of distal part of device of the FIG. 64.

FIG. 66 is a shield-side view of distal part device of the FIG. 64.

FIG. 67 is a longitudinal section view of device of the FIG. 66.

FIG. 68 is a longitudinal section view of device of the FIG. 66 with plated shield in retracted position.

DETAILED DESCRIPTION OF PREFERRED EMBODIMENTS

Figure 3:
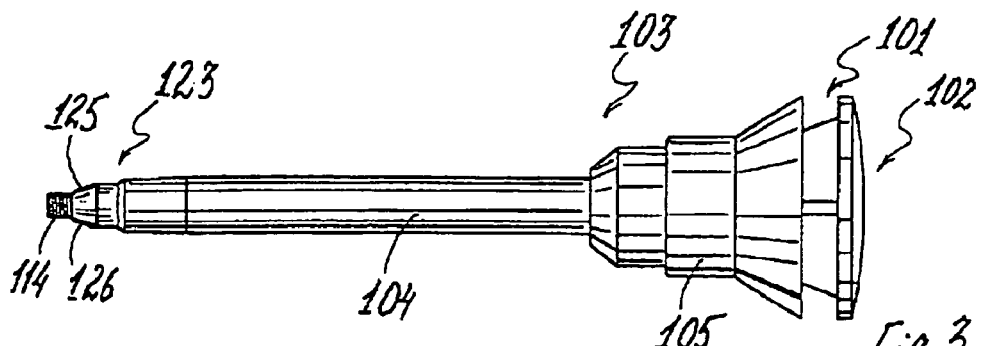
FIG. 3 is a perspective view of trocar assembly with spring penetrating apex shield.

Safety trocar assembly is intended for making orifices in body cavity wall and generation of conditions for subsequent introduction of instruments into a body cavity.

Before addressing specific implementations of the present invention in detail, it should be noted that the invention will be presented with reference to numerous examples, each of which illustrates one or more preferred feature of the invention. These various preferred features may each be used individually to advantage with an otherwise conventional trocar. In most preferred implementations, however, multiple preferred features are combined to provide a trocar with greatly enhanced levels of safety to the patient and/or professional staff, and/or to provide numerous other advantages as will become clear from the following description.

Turning now to the Figures, FIGS. 1 and 2 illustrate a first embodiment of a trocar assembly 1 in which a retractable shield 14 is deployed to selectively shield only the distal portion of a penetrating end 10. As a result, the shield extends itself as soon as the distal portion clears the tissue wall, well before fill penetration of end 10 occurs.

More specifically, FIG. 1 shows trocar assembly 1, comprising trocar unit 2 and port unit 3. FIG. 2 shows a longitudinal section of trocar assembly 1 in enlarged scale. Port unit 3 has tubular cannula 4, port housing 5 and inner seals 6, 7 located in port housing 5 and aimed to maintain insulation of the body cavity. Tubular cannula 4 has an open distal end 8. Trocar unit 2 has elongated obturator 9 adapted to be removably inserted through cannula 4 and having a penetrating end 10 exposed through cannula 4 open distal end 8. Penetrating end 10 has penetrating apex 11 and a sloping side wall 12. Longitudinal opening 17 of obturator 9 houses protector means 13 comprising tubular penetrating apex shield 14 adapted to actuate between a retracted position and an extended position (shown in FIG. 2), when shield 14 surrounds penetrating apse 11, and sloping side wall 12 surrounds shield 14 from the outside. Distal edge 15 of shield 14 forms uninterrupted hedge. Protector means 13 comprises bias means made as a compression spring 16. In the embodiment shown in FIGS. 1, 2 penetrating apex 11 formed by pointed distal edge of cylindrical piece 18, having circular ledge 19 which is abutted by circular ledge 20 of penetrating apex shield 14, when shield 14 reaches its extended position. Stopper bushing 21 abutted by spring 16 is tightly placed on proximal end of cylindrical piece 18.

Device 1 is operated as follows:

Surgeon holds device 1 by housing 5 and push member 22 situated on obturator 9 proximal end. Device 1 is oriented approximately perpendicular to body cavity wall and is pressed to it, applying pushing effort to push member 22. The resistance force of pierced tissues applied to shield distal edge 15, displaces shield 14 towards retracted position so that penetrating apex 11 strips bare and pierces body cavity wall tissues. In this process, shield uninterrupted distal edge 15 forms a hedge precluding the introduction and engagement of tissue fibers of body cavity wall between shield 14 and penetrating apex 11, thus ensuring smooth motion of device 1 through the tissues. When penetrating apex 11 and shield distal edge 15 have entered a patient's body cavity, however, before penetrating end 10 has been fully inserted the force applied to shield distal edge 15 is removed, and spring 16 returns shield 14 to extended protected position, and further movement of penetrating end 10 to body cavity occurs with protected penetrating apex 11, which precludes the injury of inner organs. Penetrating apex 11 can have diversified shapes, for instance, conical or pyramidal one, with cutting edges (not shown in the Fig.).

Turning now to FIGS. 3-6, these illustrate a variant of the embodiment of FIGS. 1 and 2 in which the shield is implemented as a helical coil of resilient wire formed with a closed portion 114 acting as the shield and a spring portion 116 which provides forward biasing. In other respects (preferred dimensions etc.), this implementation is similar to the previous embodiment. More specifically, FIG. 3 shows safety trocar assembly 101, comprising trocar unit 102 and port unit 103.

Figure 4:
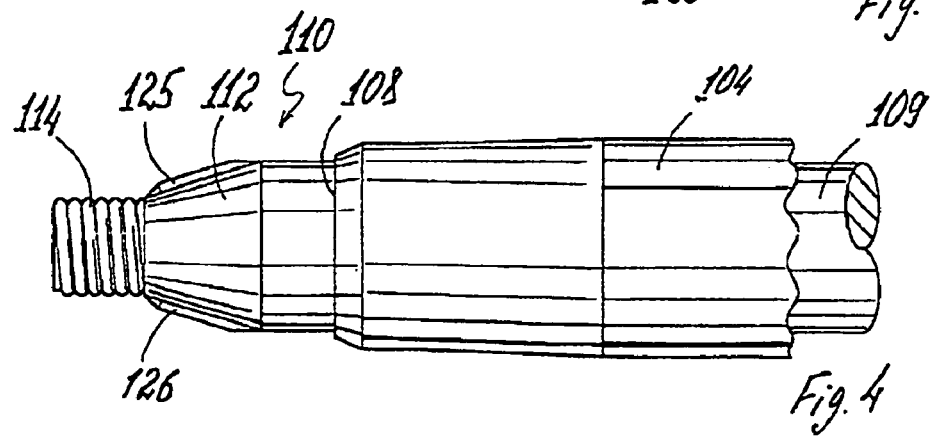
FIG. 4 is a perspective view of distal part of trocar assembly of the FIG. 3.
Figure 5:
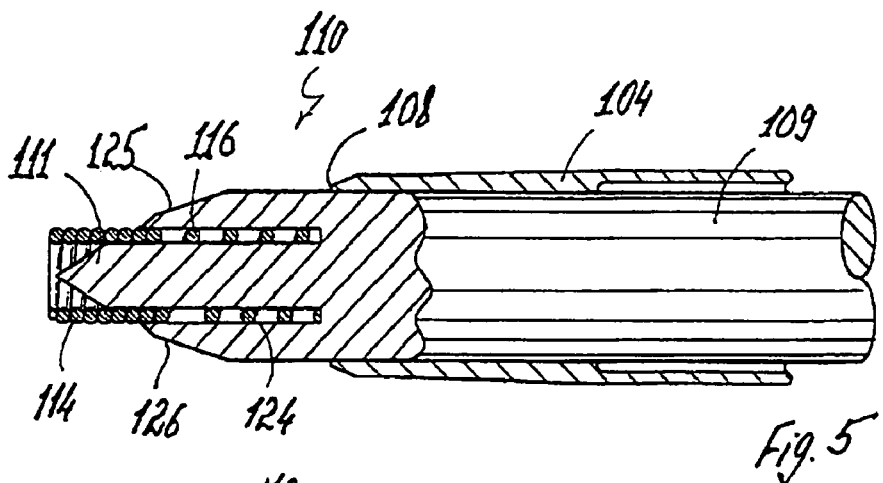
FIG. 5 is a longitudinal section of trocar assembly of the FIG. 4 and demonstrates penetrated apex shield in extended position.

FIG. 4 shows distal part 123 of device 101 in enlarged scale, and FIG. 5 shows a longitudinal section of distal part 123. Penetrating end 110, protruding through cannula 104 open distal end 108, has penetrating apex 111 made integral with obturator 109, penetrating apex shield 114, and bias means made as a compression spring 116. In this, shield 114 and spring 116 are made as a single piece from coiled springy rod fixed in obturator 109 circular groove 124. Penetrating end 110 also has sloping side wall 112, whereon outer cutting means 125, 126 made as outer cutting members are located, and which can be made of the same material as obturator 109.

FIGS. 4, 5 show shield 114 in extended protected position.

Figure 6:
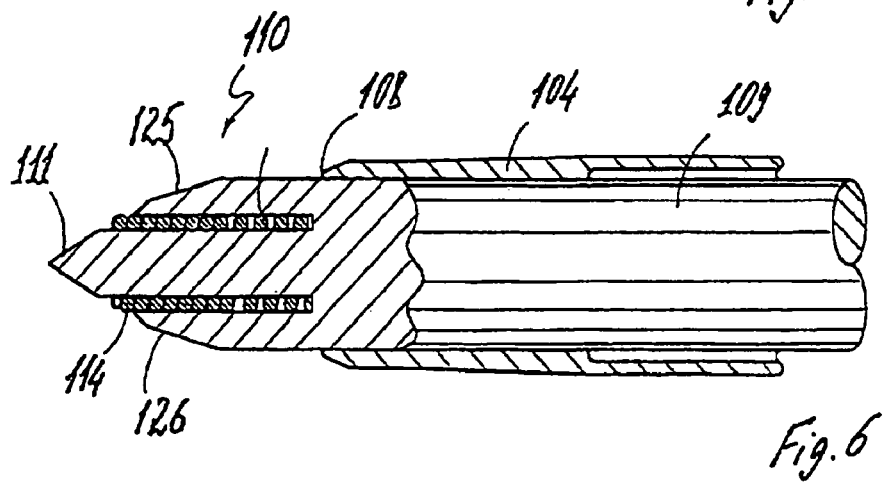
FIG. 6 is a longitudinal section of trocar assembly of the FIG. 4 and demonstrates penetrated apex shield in retracted position.

FIG. 6 shows shield 114 in retracted position

Trocar assembly 101 operates similarly to trocar assembly 1.

Turning now to FIGS. 7-14, these illustrate a similar concept as applied to a penetrating end formed as a flat knife. Specifically in relation to configurations employing cutting edges provided by flat blades, it is preferred that the shield element(s) are formed as low-profile shields in a manner that they experience very low resistance to returning to their distal protective positions almost immediately that the cutting edge clears the tissue wall.

In order to better define the preferred geometrical features which ensure this rapid return of the shield to its operative position, reference will be made in the description and claims to various terminology which is defined as follows:

the "proximal protected position" of the shield is the extreme proximal position of the shield which offers complete protection of the cutting edge.

Turning now to the structural details of this embodiment, FIG. 7 shows a safety trocar assembly 201, comprising trocar unit 202 and port unit 203.

FIG. 8 shows longitudinal section of obturator 209 distal part 227 in enlarged scale. Obturator distal part 227 comprises penetrating apex 211 with penetrating apex cutting means looking like distal knife 228 and outer cutting member looking like proximal knife 225. Both knives—228, 225—are made on the plate-shaped base 229, which has two springy arms 230, 231 with ledges 232, 233 in its proximal section, said ledges ensuring engagement of plated base 229 and obturator 209. Penetrating apex shield 214 is made as two-sided low profile shield and has longitudinal slot 234 plate base 229 passes through. Bias means is made as a compression spring 216, which abuts shield 214 with its distal face 235, whereas its proximal one abuts plate-shaped base 229. In FIGS. 7, 8, 12 shield 214 is in extended position so that its further distal displacement is limited by ledge 219 on plate-shaped base 229, which is abutted by shield 214 ledge 220. In FIGS. 13, 14 shield 214 is in acted position.

Device 201 operates similarly to device 1.

Turning now to FIGS. 15-25; these illustrate a particularly preferred embodiment which combines a distal-portion shield of the type illustrated in FIGS. 1 and 2 with a locking mechanism.

In a further preferred feature, which may be used either alone or in combination with the locking mechanism, the distal-portion shield is combined with a conventional large-diameter shield, in this case formed as concentric cylinders, to provide two-stage protection. The distal-portion shield provides immediate protection as soon as the distal portion of the penetrating end clears the tissue wall (FIG. 23), while the large-diameter shield provides additional protection once the penetrating end is fully inserted (FIG. 25). In the most preferred implementation shown here, the locking mechanism is operative to lock both shields when the obturator is removed. More specifically, FIG. 15 shows safety trocar assembly 401 with mutually independent shields 414, 436. Device 401 comprises trocar unit 402 and port unit 403. Port unit has tubular cannula 404 and port housing 405.

FIG. 16 shows a left-hand view of device 401.

FIG. 17 shows a longitudinal section view of device 401.

Trocar unit 402 has obturator 409 comprising distal part 427 and proximal part 438. Penetrating end 410 comprising penetrating apex 411, sloping side wall 412 and outer cutting members 425, 426450 with cutting edges 451 protruding above the sloping side wall 412 level. There are two tubular shields: penetrating apex shield 414 and outer shield 436. There are two independent, separate for both shields 414 and 436 bias means made as compression springs 416, 451. There is common for both shields 416, 436 lock means 435 comprising obturator-situated controlling member 440, partially protruding laterally of obturator distal part 427, and adapted to the interaction with inner surface 441 of tubular cannula 404. Controlling member is made integral with abutting member 442, having outer abutting surface 443 and inner abutting surface 452. Abutting member 442 by springy legs 444, 445 is spring-loaded to obturator 409.

FIG. 18 shows a longitudinal section of trocar unit 402 of device 401.

FIG. 19 shows top view of trocar unit 402.

In FIGS. 18, 19 lock means 435 is in lock position and locks shields 414 and 436 in protected position. Shield 436 wall has through elongated slot 446 with two different-width sections—distal section 447 is narrower than proximal section 448. Controlling member 440 has width less than that of slot 447 distal section, whereas abutting member 442 is wider than distal section 447 but narrower than slot 448 proximal section.

When trocar unit 402 is outside port unit 403 (FIGS. 18, 19), legs 444, 445 shift abutting member 442 to the lock position, when abutting member 442 partially enters slot 446 proximal section 448, and outer abutting surface 443 is set opposite of ledge 449 on outer shield 436, precluding shield 436 distal displacement, and inner abutting surface 452 is set opposite of proximal face 453 of penetrating apex shield 414, also precluding shield 414 proximal displacement. Unlocking of both shields 414, 436 occurs with trocar unit 402 entering port unit 403, which takes place when controlling member 440 interacts with cannula 404, and thus forces abutting member 442 out of interaction zone with shields 414, 436.

FIGS. 20-25 show operating shields on successive stages of penetrating end 410 passing through body cavity wall 454.

FIG. 20 shows staring moment of trocar assembly 401 interaction with body cavity walk when outer shield 436 is between its extended and retracted positions, penetrating apex shield 414 is in retracted position, and penetrating apex 411 has incorporated into body cavity wall 454.

FIG. 21 shows the moment when both shields 414, 436 are forced out by body cavity wall tissue to retracted position.

FIG. 22 shows the moment when both shields 414, 436 are in retracted position, and penetrating apex 411 has penetrated into body cavity.

FIG. 23 shows the moment immediately after the displacement of penetrating apex shield 414 to extended protected position. In this process, outer cutting members 426, 426, 450 continue cutting tissue.

FIG. 24 shows the moment before shield 436 operation.

FIG. 25 shows both shields 414, 436 in extended position.

As can be seen, independent performance of shields 414 and 436 greatly ensures trocar safe operation.

Turning now to FIGS. 26-31, these show a further embodiment of the present invention as applied to an obturator 509 with a distal knife 528. In this case, a one-sided low profile shield 514 is used. Since the cross-sectional area of the shield adds relatively little to the cross-sectional area of the knife itself, the shield advances through the incision to its distal position to provide protection almost immediately on penetration of the tissue wall. Preferably, according to the terminology defined above, the shield local comparative height along the proximal screen area for a one-sided shield is below 0.8.

FIG. 26 shows safety trocar assembly 501 with one-sided low profile shield 514. Device 501 has trocar unit 502 and port unit 503. Port unit 503 has cannula 504 and port housing 505.

FIG. 27 shows the view of device distal part 523 from the side of penetrating apex cutting means made as distal knife 528.

FIG. 28 shows left-hand view of device 501.

FIG. 29 shows device distal part 523 from the side of shield 514.

FIG. 30 shows longitudinal section of device distal part 523 when shield 514 is in extended position.

Trocar unit 502 has obturator 509 with penetrating end 510 with sloping side wall 512 and outer cutting members 525, 526 so that outer cutting members 525, 526 are made integral with obturator 509. Indented distal knife 528 is made on plate-shaped base 529, and has one-sided low profile shield 514 with bias means made as compression spring 516.

When penetrating end 510 passes through body cavity wall, the tissue resistance force shifts shield 514 to retracted position (FIG. 31), and stripped knife 528 makes an orifice in the tissue. Low profile protectors, both one-sided, and two-sided—are the protectors against instantaneous operation, i.e. they operate upon knife minimal penetration to body cavity.

FIGS. 32-41 show a further embodiment with shields for the lateral blades. Advantageously, the shield may be formed in such a manner as to provide protection for the distal portion of the blade while the proximal portion is still operative, thereby providing enhanced protection.

FIG. 32 shows safety trocar assembly 701 with one-sided low profile inverted shield 736. Device 701 has trocar unit 702 and port unit 703. Port unit 703 has cannula 704 and port housing 705. Trocar unit has obturator 709 (FIG. 34—top view of device 701 distal part 723) with penetrating end 710. Penetrating end 710 comprises blunt apex 755, sloping side wall 712, two knives 725, 725 and inverted shield 736.

FIG. 35 shows device distal part 723 from the side of knives 725, 726,

FIG. 36 shows device distal part 723 from the side of shield 736.

FIG. 37 shows longitudinal section of device 701.

FIG. 38 shows longitudinal section of device 701 trocar unit 702. Trocar assembly 701 has lock means 735 for shield 736. Lock means 735 has obturator-situated controlling member 740, partially protruding laterally of obturator 709 and adapted to the interaction with inner 740, 741 of cannula 704. Controlling member 740 is made integral with abutting member 742, having abutting surface 743. Abutting member 742 is spring-loaded to obturator 709 by springy legs 744, 745. Shield 736 has abutting bar 758. When trocar unit 702 (FIG. 38) is outside the port unit 703, legs 744, 745 shift abutting surface 743 to the level of abutting bar 758, and such mutual disposition of shield 736 and lock means 735 is the lock position which prevents shield 736 proximal displacements Unlocking of shield 736 takes place when trocar unit 702 is introduced to port unit 703 but only after protected penetrated end 710 passes through distal inner seals 706, 707 so that controlling member 740, being resisted by cannula 704 inner surface 741, shifts abutting member 742 from the interaction zone with abutting bar 758.

Figure 39:
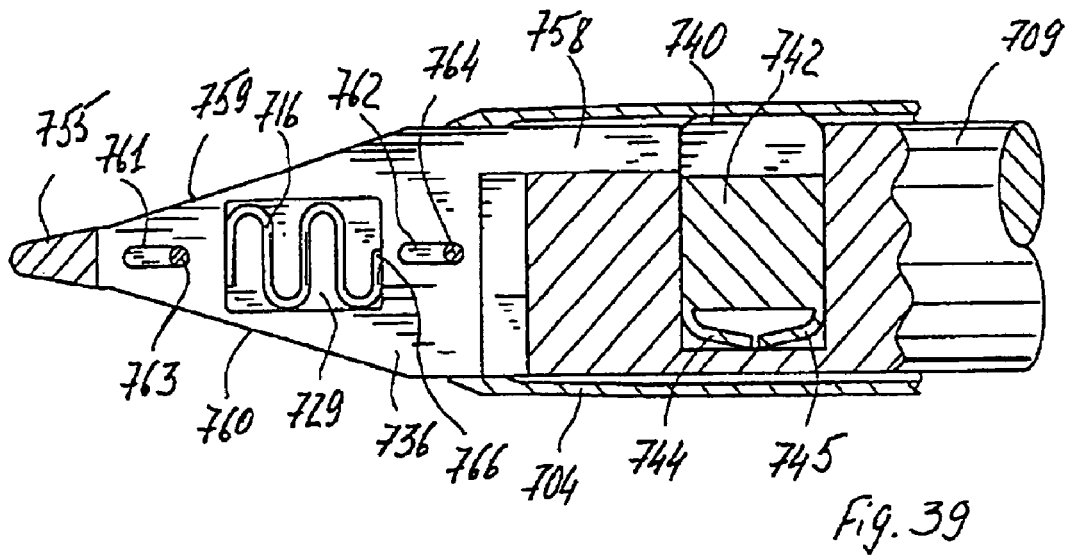
FIG. 39 is a longitudinal section of distal part of device of the FIG. 32 with shield in extended position.
Figure 40:
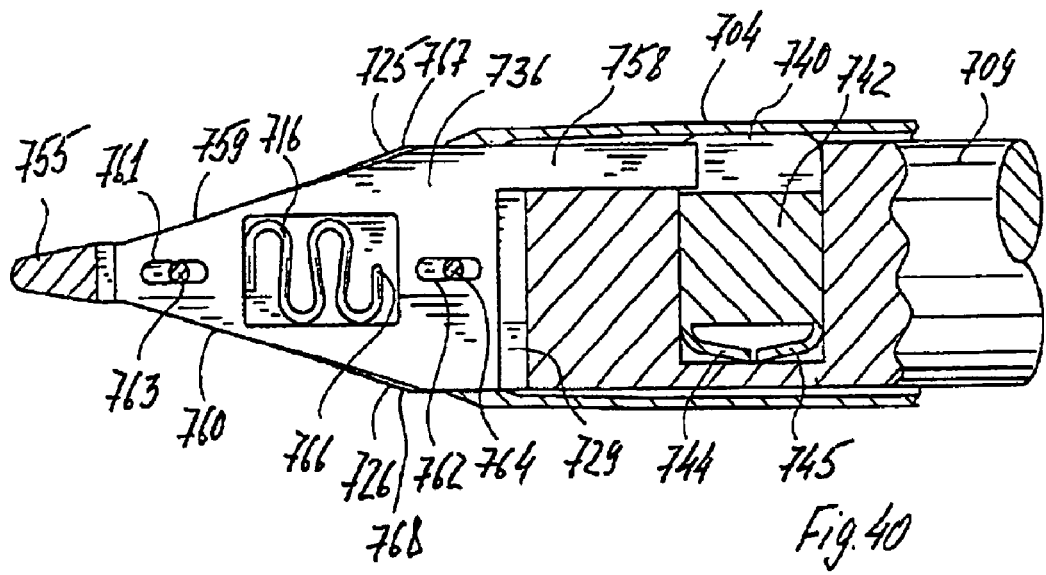
FIG. 40 is a longitudinal section of distal part of device of the FIG. 32 with shield between extended and retracted positions.
Figure 41:
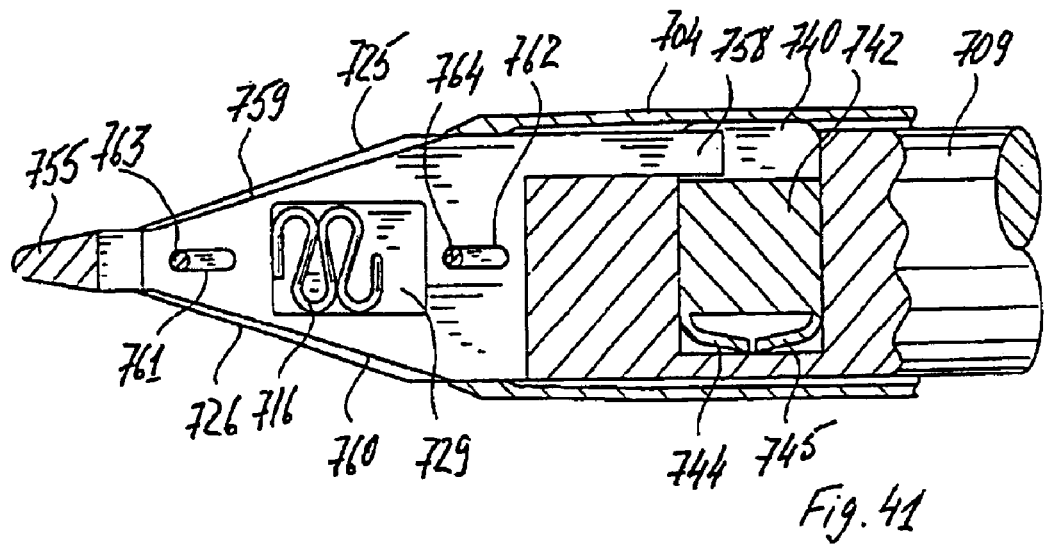
FIG. 41 is a longitudinal section of distal part of device of the FIG. 32 with shield in retracted position.

FIGS. 39, 40, 41 show longitudinal section of device 701 distal part 723 in enlarged scale at shield 736 various performance stages.

FIG. 39 shows shield 736 in extended position. Shield 736 is made plated and besides abutting bar 758 has protection edges 759, 760, guiding slots 761, 762, through which cotters 763, 764 are passing, window 765, wherein bias compression spring 716 is mounted, whose distal end abuts shield 73, whereas proximal end 766 is fixed to plate-shaped base 729 of knives 725, 726. Shield 736 is an inverted shield which means that when it shifts from extended position to retracted position, the opening of knives 725, 725 starts from their proximal sections 767, 768. This operation mechanism of shield 736 is achieved owing to the fact that relative to the device longitudinal axis the incidence angle of the line connecting distal point 769 and proximal point 770 on protection edge 759 is more acute than the incidence angle of the line connecting distal and proximal points 771, 772 on knife 725.

FIG. 41 shows shield 736 in retracted position. Consequently, as penetrating end 710 enters body cavity, closing of knives 725, 726 starts from their distal sections which ensures low injury level.

The embodiment of FIGS. 42-49 generally parallels the embodiment of FIGS. 32-41, but provides independently operative shields for the lateral blades. Thus, FIG. 42 shows a safety trocar assembly 801 with two independent low profile inverted shields 836, 871. Device 801 comprises trocar unit 802 and port unit 803. Port unit 803 comprises cannula 804 and housing 805.

FIG. 43 shows left-hand view of device 801 in enlarged scale.

FIG. 44 shows device 801 distal part 823 in enlarged scale. Trocar unit 802 comprises obturator 809 with pen ting end 810 which is formed by blunt apex 855, sloping side wall 812, with protection edges 859, 860 of shields 836, 871, and knives 825, 826 protruding above it. Shields 836, 871 are made plated and equipped with independent bias compression springs 816, 851. Knives 825, 826 (FIG. 49) are made on plate-shaped bases 829, 872.

FIGS. 45-59 show mutual arrangement of knives 825, 826 and shields 836, 871 at various operation stages of shields 836, 871. FIG. 45 shows both shields 836, 871 in extended-protected position. FIGS. 46, 47 show shields 836, 871 in intermediate position between extended and retracted position, when only proximal sections 867, 868 of knives 825, 826 are open. FIGS. 48, 49 show shields 836, 871 in retracted position, when both knives 825, 826 are open along their entire lengths.

FIGS. 45-49 show symmetrical operation of shields 836, 871, but inasmuch as shields 836, 871 are made independent and are equipped with independent bias springs 816, 851, so the operation of shields 836, 871 can be independent, non-simultaneous (not shown on Figs.). The operation non-simultaneity stems from resistance non-simultaneity of tissue elements of body cavity wall. That is the concept of independent shields permits to take into account and to respond automatically to local properties of tissues.

However, for the surgeon the mode of device 801 operation does not differ from that of similar alternative devices.

Figure 61:
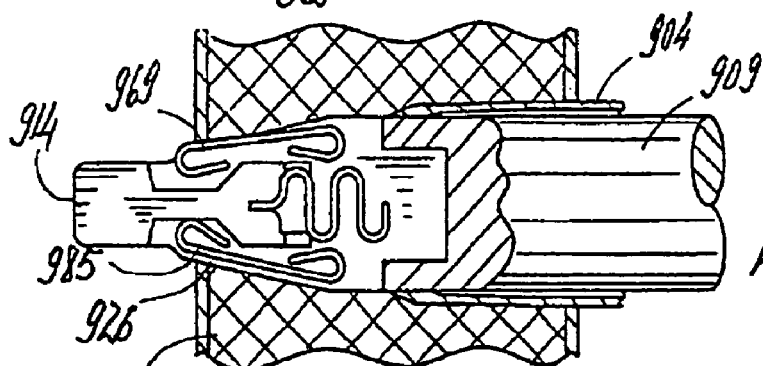
Figure 62:
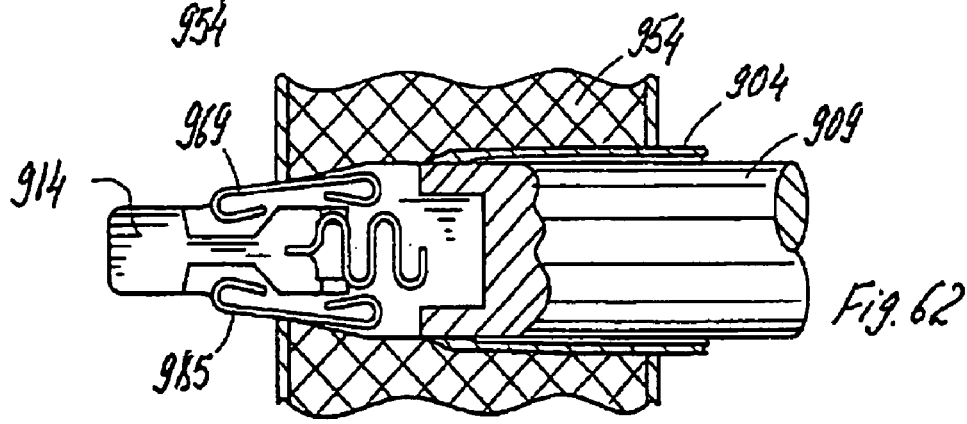

FIGS. 50-63 illustrate an alternative type of shield for lateral blades, in this case combined with a distal knife and shield similar to those of FIGS. 26-31. The lateral shields are here implemented as resilient elements which react substantially independently to force applied near their distal and proximal ends. As a result, this configuration also provides protection for the distal portion of the blades while the proximal portion is still operative (FIGS. 61 and 62). FIG. 50 shows perspective view of safety trocar assembly 901 comprising trocar unit 902 and port unit 903. Port unit 903 has cannula 904 and housing 905. Trocar unit has obturator 909 with penetrating end 910. Penetrating end is formed by sloping side wall 912, penetrating means 973 for orifice formation in body cavity wall, and protector means 913 for said penetrating means 973. Penetrating means 973 comprises penetrating zones formed by knives 928, 925, 967, 926, 968 made on common plate-sided base 929 (FIG. 53) 50 that knives 925 and 967, as well as knives 926 and 968 have cutting edges confluent with one to another. Each penetrating zone has protector member, and each protector member has its own bias member. For penetrating zone 928 made as indented knife, protector member is made as plane-shaped shield 914, whereas bias member as compression spring 916.

Protector members 969 and 970 of knives 925, 967 have bias means 951, 979, respectively, so that protector members 969, 970 are made as a common shield 936. Common shield 936 and bias means 951, 979 are made as a single resilient part, having a slat 980, which in extended position (FIGS. 51, 52, 53) is situated parallel to cutting edge of knives 925, 967, and bias means 951, 979 made as resilient elements, each of them being connected to slat 980 by one its end 981, 982, whereas the other one 983, 984 is connected to the plate-shaped base 929. Protector members 985 and 986 of knives 926 and 968 have bias means 987, 988, respectively, so that protector members 985, 986 are made as a single resilient part, having a slat 990 which in extended position is situated parallel to cutting edges of knives 926, 968, and bias means 987, 988 are made as resilient elements, each of them being connected to slat 980 by one its end 991, 992, whereas the other ones 993, 994 are connected to the plate-shaped base 929.

FIGS. 55-63 show mutual arrangement of protector members at various stages of penetrating end 910 passing through body cavity wall 954.

FIG. 55 shows shields 914, 936, 989 in extended position.

FIG. 56 shows shield 914 in retracted position, and open knife 928 creates an orifice in body tissue.

FIG. 57 shows protector members 969, 985 displaced to retracted position, and knives 925, 926 create orifice in body tissue., FIG. 58 shows all shields 914, 936, 989 in retracted positions.

FIG. 59 shows knife 928 entry to body cavity.

Figure 60:
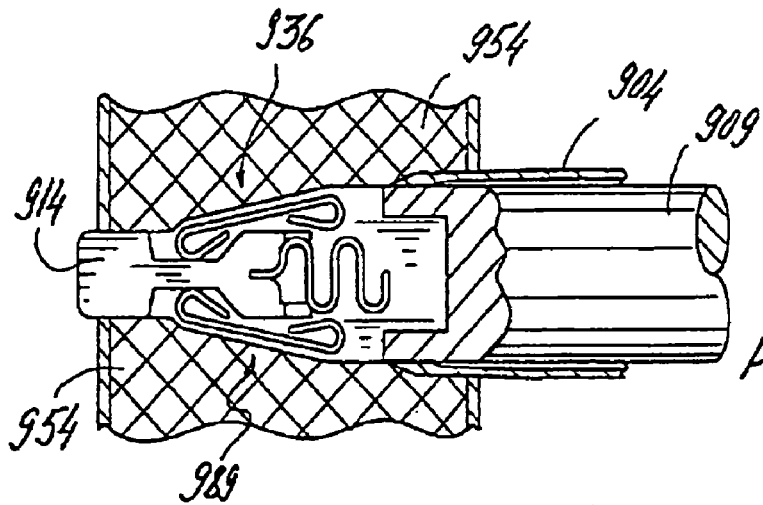

FIG. 60 shows the point immediately after shield 914 displacement to extended protected position.

FIG. 61 shows knives 925 and 926 entry to body cavity, one of them 925 being shown protected by protector member 969, which displays independent operation of symmetrical protector members 969 and 985, thus ensuring maximal fast operation of protector members, and, consequently, minimal injury of internal organs.

FIG. 62 shows protector members 914, 969, 985 in extended-protected position.

Figure 63:
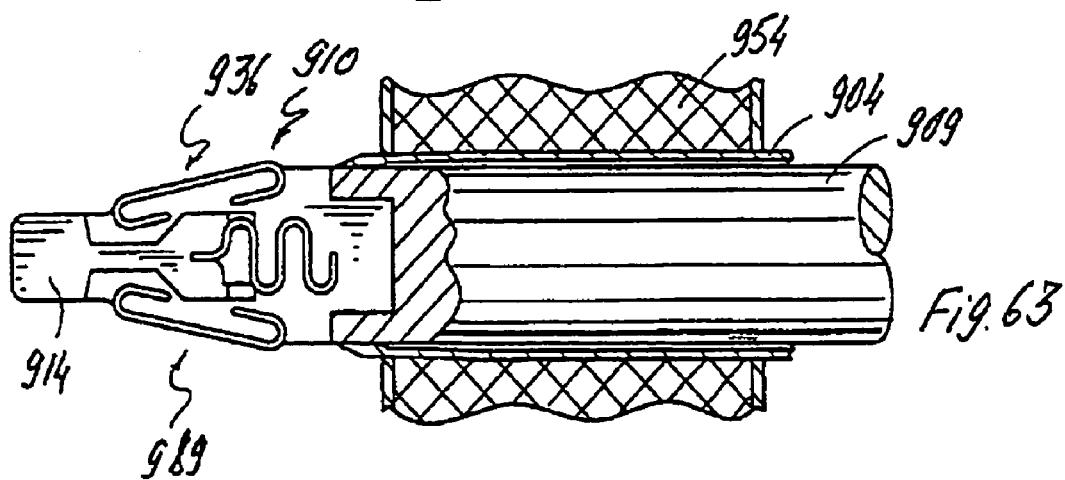
Figure 69:
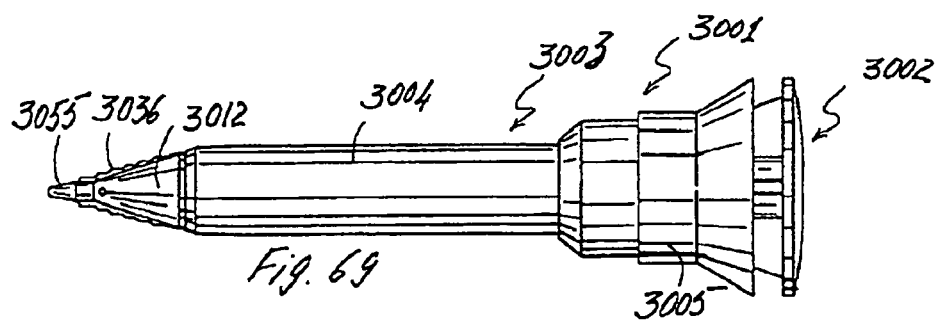
FIG. 69 is a perspective view of trocar assembly with low profile inverted stepwise shield.

FIG. 63 shows penetrating end 910 as totally entering the body cavity, with totally protected penetrating means.

FIGS. 64-68 show an embodiment generally similar to that of FIGS. 50-53, but wherein the resilient elements are formed with greater spring resistance at their rear proximal end than at their distal end, thereby also tending to preclude over-widening of the incision.

FIG. 64 shows a safety trocar assembly 2001 comprising trocar unit 2002 and port unit 2003. Port unit 2003 has cannula 2004 and housing 2005. Trocar unit has obturator 2009 with penetrating end 2010. Penetrating end is formed by sloping side wall 2012, penetrating means 2073 for orifice formation in body cavity wall, and protector means 2013 for said penetrating means 2073. Penetrating means 2073 comprises penetrating zones formed by knives 2028, 2025, 2067, 2026, 2068 made on common plate-sided base 2029 (FIGS. 65, 67) so that knives 2025 and 2067, as well as knives 2026 and 2068 have cutting edges confluent into each other. Each penetrating zone has protector member, and each protector member has its own bias member. For penetrating zone 2028 made as indented knife, protector member is made as plate-shaped shield 2014, and bias member is made as compression spring 2016.

Protector members 2069 and 2070 of knives 2025, 2067 have bias means 2056, 2079, respectively, so that protector members 2069, 2070 as made as a common shield 2036. Common shield 2036 and bias means 2051, 2079 are made as a single resilient part, having a slat 2080, which in extended position (FIGS. 64, 65) is situated parallel to cutting edges of knives 2025, 2067, and bias means 2051, 2079 are made as resilient elements, each of them being connected to slat 2080 by one its end 2081, 2082, whereas the other one 2083, 2084 is connected to the plate-shaped base 2029. Protector members 2085 and 2086 of knives 2026 and 2068 have bias means 2087, 2088, respectively, so that protector members 2085, 2086 are made as a common shield 2089. Common shield 2089 and bias means 2087, 2088 are made as a single resilient part, having a slat 2090, which in extended position is situated parallel to cutting edges of knives 2026, 2068, and bias means 2087, 2088 are made as resilient elements, each of them being connected to slat 2090 by one its end 2091, 2092, whereas the other ones 2093, 2094 are connected to the plate-shaped base 2029. In this, proximal bias means 2079 is made more rigid than distal bias means 2051, consequently, the displacement of proximal protector member 2070 and knife 2067 opening, and further on, tissue cutting at this level of penetrating means occurs at higher tissue tension than by tissue cutting at the level of knife 2025.

Shield 2089 operates in similar manner.

Such tissue cutting mechanism precludes generation of excessive diameter orifice in body cavity wall.

FIGS. 65-72 show an embodiment generally similar to that of FIGS. 32-41, in which the shield is formed with a stepped edge. The inclination of the steps to the longitudinal axis of the assembly varies from greatest at the distal part of the shield to least at the proximal part of the shield. This tends to ensure that less force is required to cause retraction of the shield at smaller diameters of hole than at large diameters, thereby limiting over-widening of the incision. Thus, FIG. 82 shows safety trocar assembly 3001 with low profile inverted shield 3036. Device 3001 has trocar assembly 3002 and port assembly 3003. Port assembly 3003 has cannula 3004, and housing 3005. Trocar assembly has obturator 3009 with penetrating end 3010 formed by blunt apex 3055, and sloping side wall 3012, with protector edges 3059, 3060 of shield 3036 and knives 3025, 3026 protruding over it.

Trocar assembly 3001 has lock means 3035 for shield 3036. Lock means 3035 has obturator-situated controlling member 3040, partially protruding laterally of obturator 3009, and adapted to the interaction with inner surface 3041 of cannula 3004. Controlling member 3040 is made integral with cutting member 3042, having abutting surface 3043. Abutting member 3042 by springy legs 3044, 3045 is spring-loaded to obturator 3009. Shield 3036 has abutting bar 3058. When trocar unit 3002 is outside port unit 3003, legs 3044, 3045 shift abutting surface 3043 to the level of abutting bar 3058, and such mutual arrangement of shield 3036 and lock means 3035 is the lock position (not shown in the Fig.), wherefrom shield 3036 proximal displacement is impossible.

Figure 70:
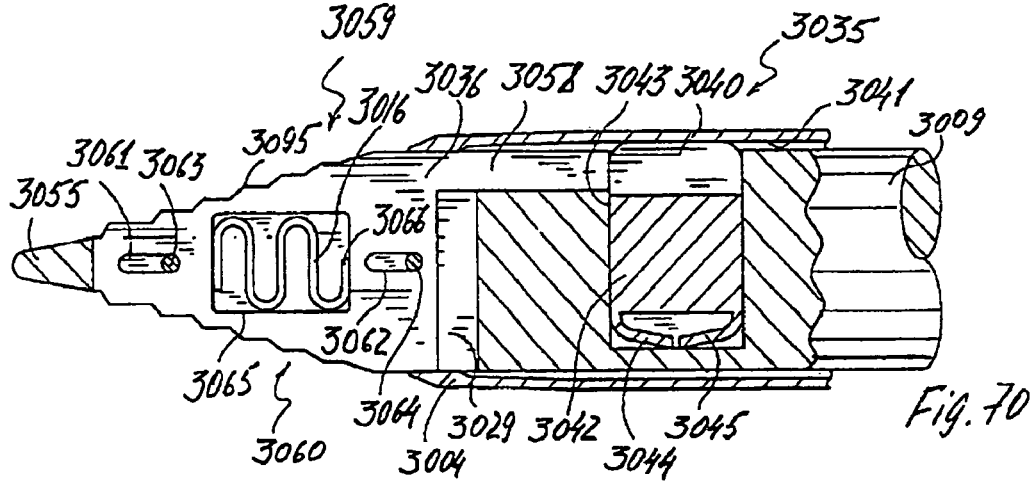
FIGS. 70-72 demonstrate the displacement stages of shield of device of the FIG. 69 from extended to retracted position.
Figure 71:
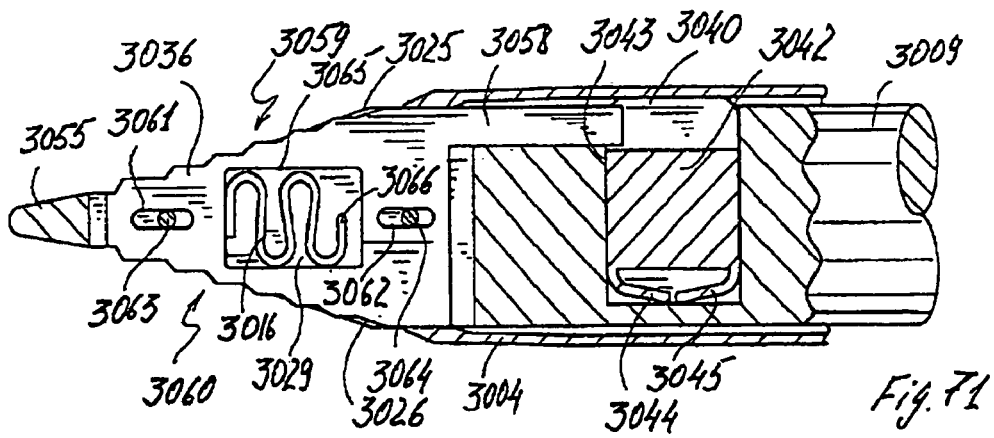
Figure 72:
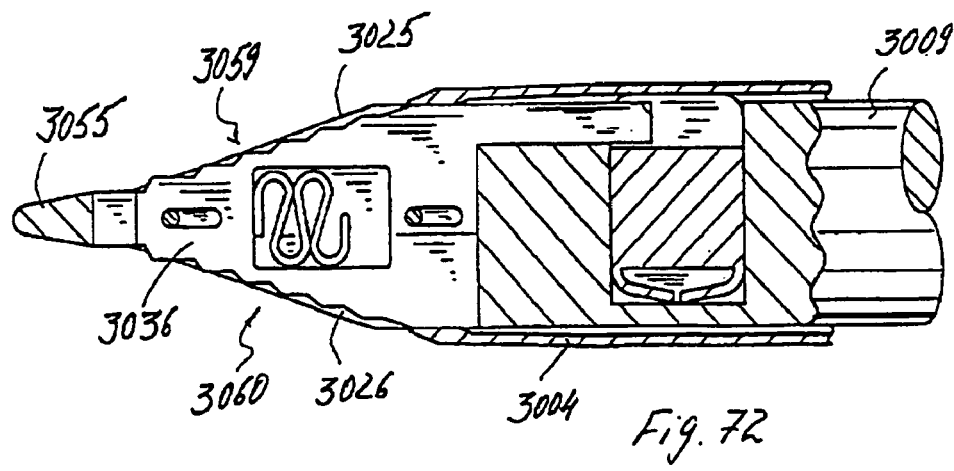

FIGS. 70, 71, 72 show longitudinal section of device 3001 distal part 3023 in enlarged scale at various stages of shield 3036 operation FIG. 70 shows shield 3036 in extended position. Shield 3036 is made plated and has, in addition to abutting bar 3058 and protection edges 3059, 3060, guiding slots 3061, 3062, through which cotters 3063, 3064 are passing, window 3065, wherein bias compression spring 3016 is mounted, abutting shield 3036 by its distal end, and fixed to plate-shaped base 3029 by its proximal end.

FIG. 70 shows shield 3036 in the position intermediate between extended and retracted ones.

FIG. 71 shows shield in retracted position.

Protector edges 3059, 3060 are made stepwise with varying slope of steps 3095 so that in distal-proximal direction the slope of steps 3095 relative to device 3001 longitudinal axis decreases, and, consequently, in the same direction decreases the force of steps 3095 engagement with the tissue, hence, larger tension is required for shield 3036 proximal displacement upon tissue interaction with proximal steps than it is for tissue interaction with distal steps, and hence, cutting of tissue at the level of distal sections 3025, 3026 occurs with smaller tissue tension than at the level of proximal sections of knives 3025, 3026. Such tissue cutting mechanism precludes generation of excessive diameter orifice in body cavity wall.

Although the present invention has been shown and described in terms of preferred embodiments, it will be appreciated that various changes and other modifications are contemplated within the spirit and scope of the present invention as defined by the following.

What is claimed is:

1. A safety trocar assembly comprising:

a trocar unit having an elongated obturator with a penetrating distal end; and a port unit with an elongated tubular cannula, having an open distal end through which said penetrating distal end of said obturator is exposed, wherein said obturator further comprises a penetrating means for orifice formation in a body cavity wall disposed onto said penetrating distal end, said penetrating means having at least two penetrating zones in the form of 1) a distal penetrating zone configured to initiate cavity wall penetration by forming an orifice in a body and firstly entering a body cavity through said orifice, and 2) a proximal penetrating zone configured to enlarge said orifice formed by said distal penetrating zone, a protector means, having at least a distal independent protector member and a proximal independent protector member for independent protection of each of said distal and proximal penetrating zones respectively during said cavity wall perforation, and a resilient bias means for each of said protector members, said bias means enabling said protector members to move independently of each other from an extended position to a retracted position in response to a resistance from perforated tissue encountered by said protector members, and to move independently of each other from said retracted position to said extended position when said resistance from perforated tissue is no longer encountered by said protector members after said penetrating zones have entered said body cavity.

2. An assembly according to claim 1, wherein said distal penetrating zone is disposed onto said penetrating distal end more distally than said proximal penetrating zone.

3. An assembly according to claim 2, wherein said distal protector member protects said distal penetrating zone, and wherein said proximal protector member protects both of said penetrating zones.

4. An assembly according to claims 3, wherein said proximal shield envelops, in its extended position, said distal protector member and both of said penetrating zones.

5. An assembly according to claims 4, wherein said proximal shield is tubular.

6. An assembly according to claim 1, wherein each of said penetrating zones is in propinquity to a cutting member, and wherein said independent protector members are made as separate shields.

* * * * *